(12) United States Patent
Dore et al.

(10) Patent No.: US 8,173,620 B2
(45) Date of Patent: May 8, 2012

(54) BHQ-CAGED NUCLEOTIDE PROBES PHOTOLYSABLE BY TWO-PHOTON EXCITATION

(75) Inventors: Timothy M. Dore, Athens, GA (US); Yue Zhu, Changchun (CN); Khalilah G. Reddie, Ann Arbor, MI (US); James D. Lauderdale, Statham, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 319 days.

(21) Appl. No.: 12/544,523

(22) Filed: Aug. 20, 2009

(65) Prior Publication Data

US 2010/0048502 A1 Feb. 25, 2010

Related U.S. Application Data

(60) Provisional application No. 61/090,400, filed on Aug. 20, 2008, provisional application No. 61/105,130, filed on Oct. 14, 2008.

(51) Int. Cl.
*A01N 43/04* (2006.01)
*A61K 31/70* (2006.01)

(52) U.S. Cl. ............... 514/47; 514/43; 514/45; 514/46; 514/49; 514/50; 514/51; 536/25.3; 536/27.1; 536/27.13; 536/28.1

(58) Field of Classification Search .................. None
See application file for complete search history.

(56) References Cited

PUBLICATIONS

Fedoryak et al. Organic Letters (2002), vol. 4, pp. 3419-3422.*

* cited by examiner

*Primary Examiner* — Patrick Lewis
(74) *Attorney, Agent, or Firm* — Thomas, Kayden, Horstemeyer & Risley, LLP

(57) ABSTRACT

The disclosure encompasses caged compounds such as caged nucleoside phosphoesters (caged nucleotides). In an embodiment, the caged nucleotides include compounds corresponding to those described by formula (I) that may be activated by two-photon excitation, and methods of synthesis of such compounds. 8-Bromo-7-hydroxyquinoline-caged ATP was synthesized and examined for its photochemistry as a biologically useful, temporally and spatially controlled ATP-releasing reagent. The combination of two-photon excitation hydrolysis and activation of caged ATP enables methods for finely focusing ATP activation at the sub-cellular level or to a greater depth of activation, thereby providing improved resolution of ATP-dependent processes at the cellular level.

20 Claims, 26 Drawing Sheets

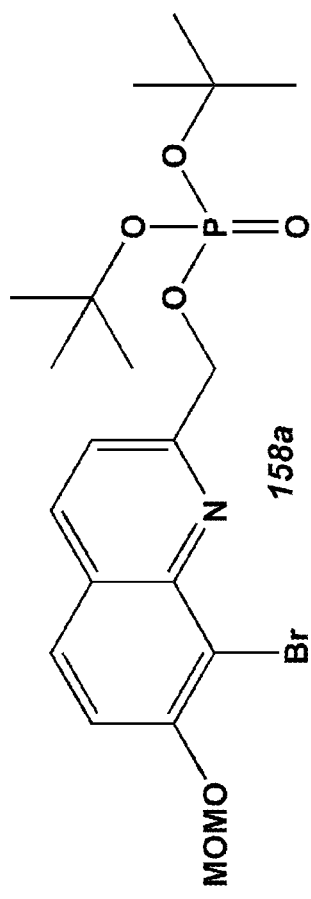
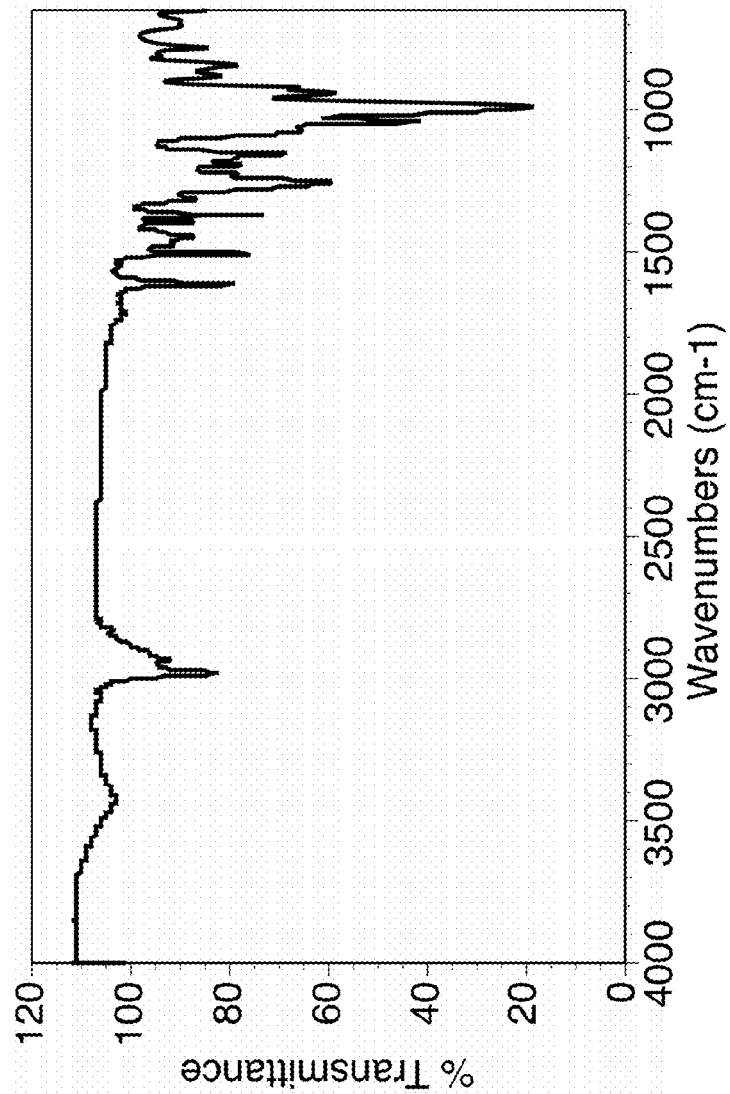
Fig. 9

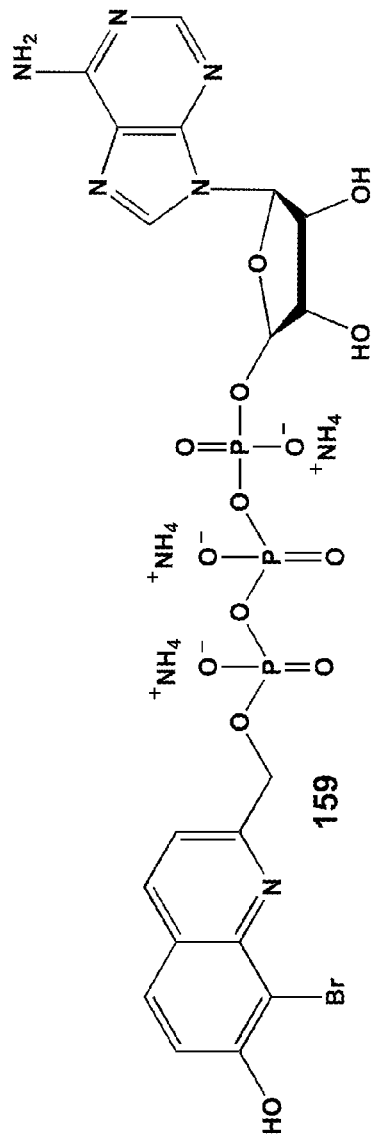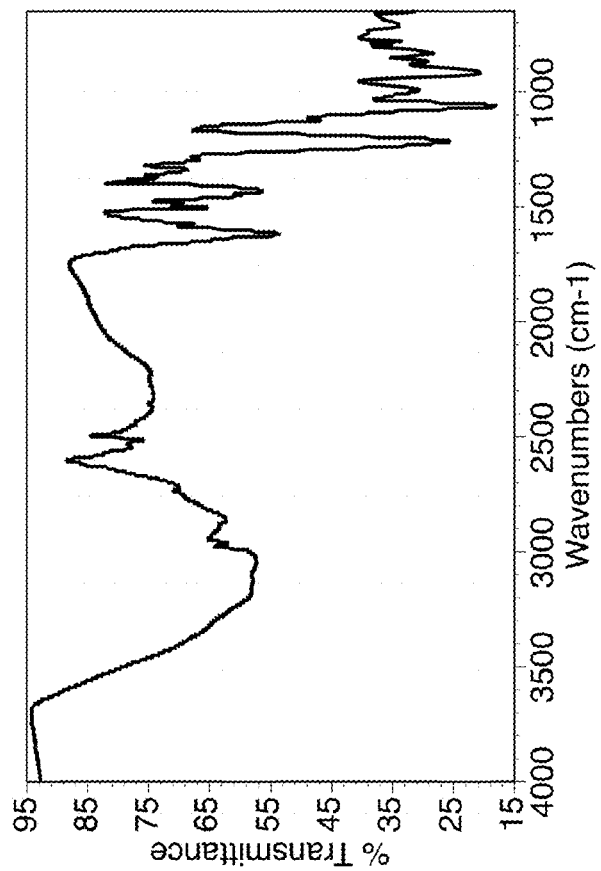
Fig. 16

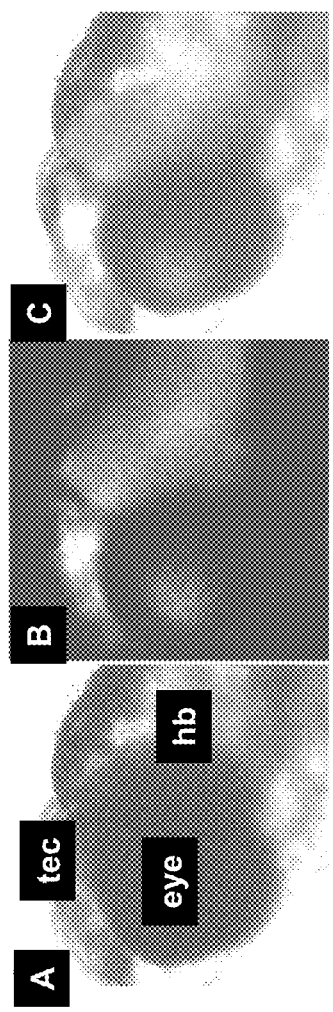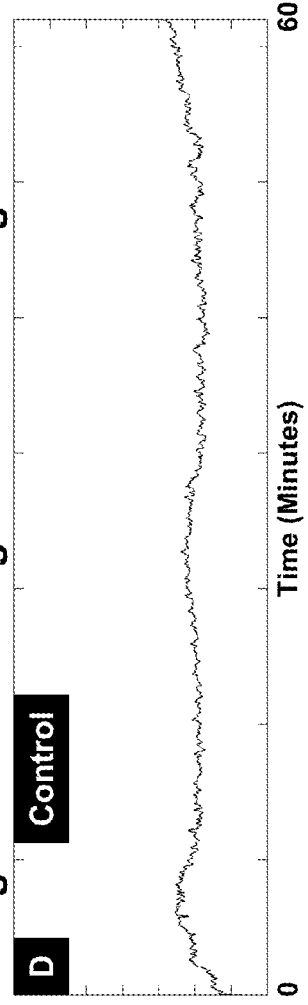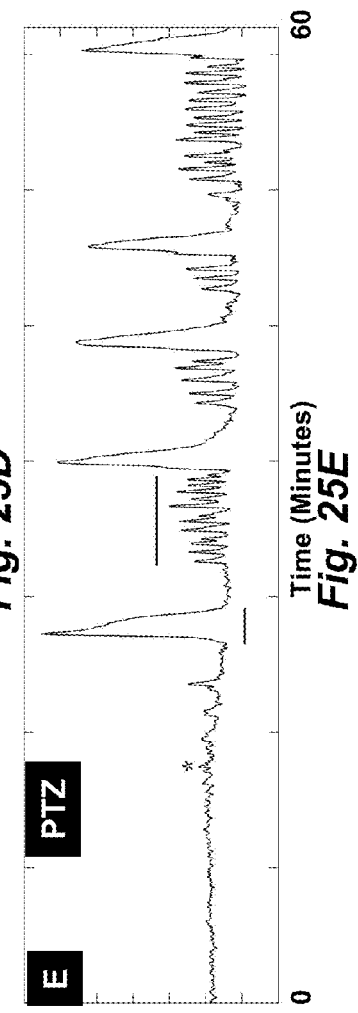

BHQ-CAGED NUCLEOTIDE PROBES PHOTOLYSABLE BY TWO-PHOTON EXCITATION

CROSS-REFERENCE TO RELATED APPLICATIONS

This application claims priority to U.S. Provisional Patent Application Ser. Nos. 61/090,400, entitled "PHOTON-ACTIVATABLE ATP-RELEASING COMPOUND" filed on Aug. 20, 2008, and 61/105,130, entitled "BHQ-GATED NUCLEOTIDE PROBES PHOTOLYSABLE BY TWO-PHOTON EXCITATION" filed on Oct. 14, 2008, the entireties of which are hereby incorporated by reference.

STATEMENT REGARDING FEDERALLY SPONSORED RESEARCH OR DEVELOPMENT

This invention was made with government support under NSF Grant No. CHE-0349059 awarded by the U.S. National Science Foundation of the United States government. The government has certain rights in the invention

TECHNICAL FIELD

The present disclosure is generally related to caged nucleotides that can be selectively photolysed by two-photon excitation. The present disclosure is further related to methods of synthesis of caged nucleotides.

BACKGROUND

ATP is a unique chemical energy carrier in most energy-requiring processes. The solvolysis of ATP will release energy, and the process has been involved in active transport, in muscle contraction, endo- and exocytosis, cytoplasmic streaming, ciliary movements, conformational changes of proteins, and multiple other dynamic biological processes. The first caged compound produced was the 2-nitrobenzyl ester of ATP (NB-ATP) (Kaplan et al., Biochemistry (1978), 77: 1929-1935). Biologists and physiologists have used analogs of NB to cage ATP (Kaplan et al., Biochemistry (1978), 77: 1929-1935; Walker, Reid et al., J. Am. Chem. Soc. (1988), 770: 7170-7177; Haugland et al. U.S. Pat. No. 5,635,608), which are the only commercially available caged ATPs. Available caged ATPs include $N^6$-(2,4-Dinitrophenyl) ester of ATP (DNP-caged ATP) (Corrie et al., in *Biological Applications of Photochemical Switches*', Morrison, H., Ed.; John Wiley & Sons: New York, (1994), pp 243-305); benzoin-ATP (Givens & Park, Tetrahedron Lett. (1996), 37: 6259-6262); $P^3$-[1-(3,5-dimethoxyphenyl)-2-phenyl-2-oxo]ethyl ester of ATP (DMB-caged ATP) (Sokolov et al., Biophys. J. (1998), 74: 2285-2298); $P^3$-[2-(4-hydroxyphenyl)-2-oxo]ethyl ATP (pHP-caged ATP) (Park & Givens, J. Am. Chem. Soc. (1997), 119: 2453-2463), and [7-(dimethylamino)coumarin-4-yl] methyl ATP (DMACM-ATP) (Geissler et al., Chembiochem. (2003), 4: 162-170). All of these molecules possess a covalent bond to the $P^3$ phosphate group of ATP to ensure that the biological activity of ATP is rendered inert.

The first synthetic caged compound, NB-ATP, was synthesized and its biological use as a controllable source of ATP was illustrated by Kaplan et al., (Biochem. (1978), 77: 1929-1935). Incubated with renal Na,K-ATPase (a membrane protein that hydrolyzes ATP to drive the coupled extrusion and uptake of $Na^+$ and $K^+$ ions through the plasma membrane), NB-ATP was neither a substrate nor inhibitor of this enzyme. Upon irradiation, however, ATP was released and activated the pump.

DMB-ATP was also used (Sokolov et al., Biophys. J. (1998), 74: 2285-2298) to study electrogenic ion transport by Na,K-ATPase. In this case, DMB-ATP was selected over $P^3$-1-(2-nitrophenyl)ethyl ester of ATP (NPE-caged ATP) because DMB-ATP has an ATP release rate $>10^5$ $sec^{-1}$, while the ATP release rate of NPE-ATP is 118 $sec^{-1}$. The liberated ATP activated the pump for $Na^+$ transport. Transient currents in the system were recorded and analyzed to determine that the rate constants of enzyme phosphorylation and ADP-dependent dephosphorylation were 600 $sec^{-1}$ and $1.5 \times 10^6$ $M^{-1} \cdot sec^{-1}$.

DMACM-caged ATP was synthesized to provide a tool that had an efficient photorelease of ATP at long wavelengths and fast release of ATP ($1.6 \times 10^9$ $sec^{-1}$). In cultures of mouse astrocytes and in brain tissue slices from mice, the DMACM-caged ATP was irradiated, and the release of ATP evoked $Ca^{2+}$ ion waves.

SUMMARY

Briefly described, embodiments of this disclosure, among others, encompass caged nucleoside phosphoesters (caged nucleotides) such as compounds corresponding to those described by formula (I) that may be activated by two-photon excitation, and methods for the synthesis of such compounds. Embodiments further encompass methods of detecting in biochemical and physiological reactions initiated by the photolytic uncaging of a moiety such as, but not limited to, a nucleotide, and acetyl group and the like. 8-Bromo-7-hydroxyquinoline-caged ATP was synthesized and examined for its photochemistry as a biologically useful, temporally and spatially controlled ATP-releasing reagent. The combination of two-photon excitation hydrolysis and activation of caged ATP enables methods for finely focusing ATP activation at the sub-cellular level or to a greater depth of activation, thereby providing improved resolution of ATP-dependent processes at the cellular level. One aspect of the disclosure, therefore, provides caged nucleoside phosphoesters that may be activated by two-photon excitation, and methods of synthesis. In embodiments of the disclosure, caged nucleosides such as, but not limited to, ATP are provided where the blocking (gating) moiety coupled to the nucleoside may be a variant of hydroquinoline, and in particular 8-bromo-7-hydroxyquinoline. One embodiment of the disclosure provides 8-bromo-7-hydroxyquinoline-ATP.

Accordingly, the disclosure encompasses compounds having the formula:

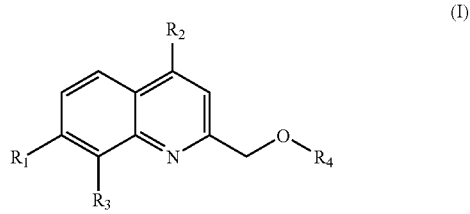

where $R_1$ can be selected from the group consisting of: HO—, HS—, and $(Me)_2N$—; $R_2$ can be selected from the group consisting of: H and Cl; $R_3$ can be selected from the group consisting of: H, $NO_2$, CN, Cl, and Br; and $R_4$ can be selected from the group consisting of: acetyl- and a nucleoside phosphoester. In embodiments of this aspect of the disclosure, the nucleoside phosphoester can be selected from the group consisting of: adenosine monophosphate (AMP), adenosine diphosphate (ADP), adenosine triphosphate (ATP), cytosine monophosphate (CMP), cytosine diphosphate (CDP), cytosine triphosphate (CTP), guanine monophosphate (GMP), guanine diphosphate (GDP), guanine triphosphate (GTP), thymidine monophosphate (TMP), thymidine diphosphate (TDP), and thymidine triphosphate (TTP).

In one embodiment, the compound is 8-Bromo-7-hydroxyquinoline-ATP and can have the formula:

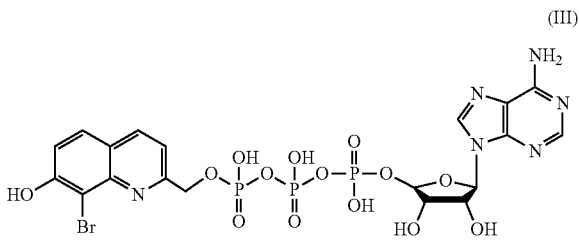

(III)

Another aspect of the disclosure provides methods of synthesizing a caged nucleoside, comprising: (a) protecting the free hydroxy group of BHQ with a protecting group; (b) synthesizing a protected BHQ-alcohol; (c) synthesizing a protected BHQ-phosphate from the protected BHQ-alcohol, wherein the phosphate has protecting groups thereon; (d) removing the protecting groups from the protected BHQ-phosphate; (e) coupling of the BHQ-phosphate and an activated nucleotide; and (f) isolating a BHQ-nucleotide. In one embodiment of the methods of this aspect of the disclosure, the activated ADP can be ADP-imidazolide and the BHQ-nucleotide can be BHQ-ATP (III).

Yet another aspect of the disclosure provides for methods of detecting a biochemical or physiological reaction in a biological sample, comprising the steps of: (a) obtaining a biological sample; delivering to the biological sample a caged nucleotide; (c) irradiating the biological sample with light energy, thereby dissociating the caged nucleotide to provide an uncaged nucleotide and initiating a biochemical or physiological reaction in the biological sample; and (d) detecting the detecting the biochemical or physiological reaction in the biological sample.

In embodiments of this aspect of the disclosure, the methods may further comprise the steps of: (i) contacting the biological sample with an indicator composition, wherein the indicator composition responds to the biochemical or physiological reaction by providing an detectable signal; (ii) allowing the indicator composition to emit a detectable signal; and (iii) detecting the emitted signal, thereby detecting the biochemical or physiological reaction.

In other methods of this aspect of the disclosure, the physiological reaction can generate an electrophysiological signal, and the method may further comprise the step of detecting the electrophysiological signal.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 9 is a graph showing the FTIR spectrum for MOM-BHQ di-tert-butyl phosphate (158a).

FIG. 16 is a graph showing the FTIR spectrum for BHQ-ATP (159).

FIG. 24A shows the action of ATP at different concentrations; FIG. 24B shows the action of BHQ-ATP (100 µM) after exposure to light, compared to ATP.

FIGS. 25A-25E are digital images illustrating PTZ-induced changes in neuronal $Ca^{2+}$ in the brain of a 7 dpf zebrafish larva. (A-A") represents the region of the zebrafish imaged. FIG. 25A shows a lateral view of the head with the dorsal side up and anterior to the left. FIG. 25B shows a digital image of chameleon cyan fluorescence. FIG. 25C is a digital merged image of the images of FIGS. 25A and 25B (tec: tectum, hb: hindbrain, scale bar=150 mm). FIG. 25D is a graphical output showing neuronal $Ca^{2+}$ in the absence of PTZ. FIG. 25E is a graphical output showing neuronal $Ca^{2+}$ after 1 h of continuous exposure to 15 mM PTZ introduced at 0 min. Increase in the YFP/CFP ratio indicates an increase in intracellular $Ca^{2+}$ concentration.

Figure 1:
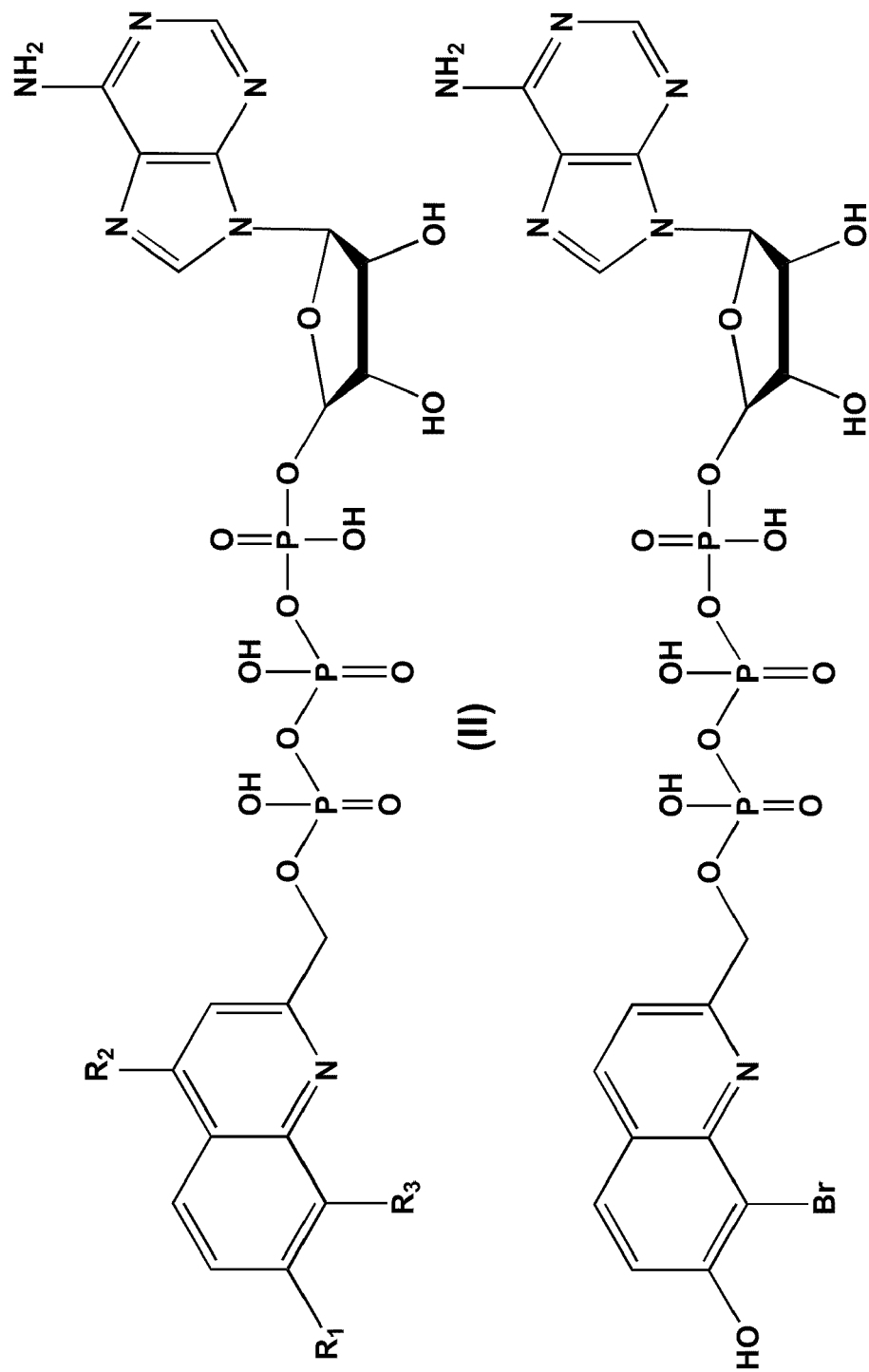
FIG. 1 illustrates the structural formulae for a generalized caged ATP structure (II), and the compound 8-bromo-7-hydroxyquinoline-ATP (BHQ-ATP (159)).

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Abbreviations:

ATP, adenosine triphosphate; ADP, adenosine diphosphate; BHQ, 8-bromo-7-hydroxyquinoline; BHQ-OAc, 8-bromo-7-hydroxyquinoline-acetate; BHQ-ATP (159), 8-bromo-7-hydroxyquinoline-ATP; MOM, methoxymethyl; FTIR, Fourier Transform Infra-Red spectroscopy; THF, tetrahydrofuran; HMPA, hexamethylphosphoramide; DMF, dimethylformamide; room temperature, room temperature.

Definitions

In describing and claiming the disclosed subject matter, the following terminology will be used in accordance with the definitions set forth below.

The term "caging group" as used herein refers to a moiety that can be employed to reversibly block, inhibit, or interfere with the activity (e.g., the biological activity) of a molecule (e.g., a polypeptide, a nucleic acid, a small molecule, a drug, and the like). Typically, one or more caging groups are associated (covalently or noncovalently) with the molecule but do not necessarily surround the molecule in a physical cage. For example, a single caging group covalently attached to a phosphate side chain of a nucleoside required for the catalytic activity of an enzyme or physiological process can block the activity of the enzyme. The enzyme would thus be caged even though not physically surrounded by the caging group. Caging groups can be, for example, relatively small moieties such as carboxyl nitrobenzyl, 2-nitrobenzyl, nitroindoline, hydroxyphenacyl, DMNPE, quinilones including bromoquinilones and derivatives thereof, or the like, or they can be, e.g., large bulky moieties such as a protein or a bead. Caging groups can be removed from a molecule, or their interference with the molecule's activity can be otherwise reversed or reduced, by exposure to an appropriate type of uncaging energy and/or exposure to an uncaging chemical, enzyme, or the like. The caging groups of the present disclosure may be released from the blocked or "caged" nucleoside triphophoester (uncoupled) by photolysis following two-photon excitation.

The terms "photoactivatable" or "photoactivated" as used herein refer to where a caging group whose blockage, inhibition of, or interference with the activity of a molecule with which the photoactivatable caging group is associated can be reversed or reduced by exposure to light of an appropriate wavelength. For example, exposure to light can disrupt a network of caging groups physically surrounding the molecule, reverse a noncovalent association with the molecule, trigger a conformational change that renders the molecule active even though still associated with the caging group, or, as with the compounds of the present disclosure, cleave a photolabile covalent attachment to the molecule. In the present disclosure, therefore, the photoactivatable caging group is released from the protected entity by two-photon laser excitation, the laser light having a wavelength greater than about 700 nm. Interchangeable with the terms "photoactivatable" or "photoactivated" as used herein is the term "photolabile" including a caging group whose covalent attachment to a molecule is reversed (cleaved) by exposure to light of an appropriate wavelength. The photolabile caging group can be, e.g., a relatively small moiety such as carboxyl nitrobenzyl, 2-nitrobenzyl, nitroindoline, hydroxyphenacyl, DMNPE, or the like, or it can be, e.g., a relatively bulky group (e.g., a macromolecule, or a protein) covalently attached to the molecule by a photolabile linker (e.g., a polypeptide linker comprising a 2-nitrophenyl glycine residue, or a substituted hydroxyquinoline such as, but not limited to, 8-Bromo-7-hydroxyquinoline).

Appropriate methods for uncaging caged molecules are also known in the art. For example, appropriate wavelengths of light for removing many photolabile groups have been described; e.g., 300-360 nm for 2-nitrobenzyl, 350 nm for benzoin esters, and 740 nm for brominated 7-hydroxycoumarin-4-ylmethyls (two-photon). Conditions for uncaging any caged molecule (e.g., the optimal wavelength for removing a photolabile caging group) can be determined according to methods well known in the art. Instrumentation and devices for delivering uncaging energy are likewise known. For example, well known and useful light sources include e.g., a lamp, a laser (e.g., a laser optically coupled to a fiber-optic delivery system) or a light-emitting compound.

The two-photon photolysis can use less energy and be less damaging to the surroundings of the compound being uncaged. A high degree of three-dimensional spatial precision can be obtained by excitation with two or more coincident infrared photons of equivalent total energy to a single photon. Such multiphoton excitation can require extremely high local intensities, typically obtained by focusing a femtosecond pulsed infrared (IR) laser with a high-numerical-aperture lens. The intensity becomes insignificant away from the point of focus. This nonlinear optical phenomenon can be used to noninvasively localize the photochemistry to any given spot in three dimensions and can be especially valuable in mapping biochemical sensitivities in complex tissues such as the brain.

Photosensitivity is quantified as the uncaging action cross-section $\delta_u$ which is the product of the two-photon absorbance cross-section $\delta_a$ and the uncaging quantum yield $Q_{u2}$. Ideally, $\delta_u$ should exceed 0.1 GM, where GM (Goeppert-Mayer) is defined as $10^{-50}$ cm$^4$s/photon. For example, carboxylate, phosphate, and carbamate esters of brominated 6-hydroxycoumarin-4-ylmethanol have the requisite action cross-sections ($\delta_u$ about 1 GM), photolysis kinetics, synthetic accessibility, water solubility, and stability in the dark to be used in the true two-photon uncaging of biologically important acids and amines. In addition, their cross-sections for one-photon uncaging with UV radiation at 365 nm or longer are high. Two-photon photolysis can lead to deeper, high-resolution and less-invasive mapping of the local responses of complex tissues to neurotransmitters and messengers, and the like.

The term "nucleobase" as used herein refers to a nitrogen-containing heterocyclic moiety capable of forming Watson-Crick type hydrogen bonds with a complementary nucleobase or nucleobase analog, e.g., a purine, a 7-deazapurine, or a pyrimidine. Typical nucleobases are the naturally occurring nucleobases adenine, guanine, cytosine, uracil, thymine, and analogs of naturally occurring nucleobases, e.g., 7-deazaadenine, 7-deaza-8-azaadenine, 7-deazaguanine, 7-deaza-8-azaguanine, inosine, nebularine, nitropyrrole, nitroindole, 2-amino-purine, 2,6-diamino-purine, hypoxanthine, pseudouridine, pseudocytidine, pseudoisocytidine, 5-propynyl-cytidine, isocytidine, isoguanine, 2-thiopyrimidine, 6-thioguanine, 4-thiothymine, 4-thiouracil, $O_6$-methylguanine, $N_6$-methyl-adenine, $O^4$-methylthymine, 5,6-dihydrothymine, 5,6-dihydrouracil, 4-methylindole, ethenoadenine, and the like.

The term "nucleoside" as used herein refers to a compound comprising a nucleobase linked to a C-1' carbon of a ribose sugar or analog thereof. The ribose or analog may be substituted or unsubstituted. Substituted ribose sugars include, but are not limited to, those riboses in which one or more of the carbon atoms, preferably the 3'-carbon atom, is substituted with one or more of the same or different substituents such as —R, —OR, —NRR or halogen (e.g., fluoro, chloro, bromo, or iodo), where each R group is independently —H, $C_1$-$C_6$ alkyl or $C_3$-$C_{14}$ aryl. Particularly preferred riboses are ribose, 2'-deoxyribose, 2',3'-dideoxyribose, 3'-haloribose (such as 3'-fluororibose or 3'-chlororibose) and 3'-alkylribose. Typically, when the nucleobase is A or G, the ribose sugar is attached to the $N^9$-position of the nucleobase. When the nucleobase is C, T or U, the pentose sugar is attached to the $N^1$-position of the nucleobase.

The term "nucleotide" as used herein refers to a phosphate ester of a nucleoside, either as an independent monomer or as a subunit within a polynucleotide. Nucleotide triphosphates are sometimes denoted as "NTP", "dNTP" (2'-deoxypentose) or "ddNTP" (2',3'-dideoxypentose) to particularly point out the structural features of the ribose sugar. "Nucleotide 5'-triphosphate" refers to a nucleotide with a triphosphate ester group at the 5' position. The triphosphate ester group may include sulfur substitutions for one or more phosphate oxygen atoms, e.g., α-thionucleotide 5'-triphosphates.

The term "biological sample" as used herein refers to any sample of biological origin including whole living or deceased animals, human or plants, a tissue sample or a cell sample therefrom. The tissue sample can comprise blood, saliva, semen, muscle or from any internal organs. In the methods of the present disclosure, the source of the tissue sample is not critical. A body fluid may be selected from the group consisting of blood, ascites, pleural fluid and spinal fluid, and the like. Whatever source of cells or tissue is used, a sufficient amount of cells must be obtained to provide a sufficient amount of the desired analysis. This amount will be known or readily determinable by those skilled in the art.

The term "pharmaceutically acceptable carrier" as used herein refers to a diluent, adjuvant, excipient, or vehicle with which a caged compound of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a subject, the caged compound and pharmaceutically acceptable carriers can be sterile. Water is a useful carrier when the caged compound is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

The term "pharmaceutically acceptable" as used herein refers to a compound or combination of compounds that while biologically active will not damage the physiology of the recipient human or animal to the extent that the viability of the recipient is comprised. Preferably, the administered compound or combination of compounds will elicit, at most, a temporary detrimental effect on the health of the recipient human or animal is reduced.

The term "light energy" as used herein refers to a laser generated light having a wavelength of between about 300 nm and 800 nm, but having a wavelength capable of generating cleavage of a chemical bond by either one or two photon laser excitation.

The term "biochemical" as used herein refers to chemical reactions typically associated with the processes to maintain the viability and/or reproduction of a living cell or organism.

The term "physiological" as used herein refers to processes combining a variety of biochemical, physical, cellular processes and the like that result in the normal or pathological status of a living cell or organism, The term "electrophysiological" as used herein refers to the electrical currents generated by physiological and/or biochemical changes in neural and muscular tissues of an animal.

The term "metabolite" as used herein refers to a compound generated as a result of the functioning of a biochemical reaction in a cell or organism. A metabolite may be transient and rapidly converted to a chemically related or unrelated compound, or may be the end-product of a series of biochemical reactions.

Description

The present disclosure encompasses caged nucleosides, including, but not limited to, a caged ATP, and variants thereof, that may be used, for example, in metabolic studies of single cells, cultured cells, cells in vivo in a tissue, whole animals (e.g., zebrafish), and the like, by two-photon excitation. It is within the scope of the disclosure, however, for any nucleoside phosphoester to have a blocking, or gating, group attached thereto to inhibit a biochemical or physiological function of the nucleoside phosphoester.

Caged compounds have been used in biochemistry and physiology for over two decades. BHQ compounds were found to protect bioactive functional groups and release the substrate effectively upon irradiation of light. BHQ-protected carboxylates, phosphates, and glycerol derivatives were synthesized and tested for their photochemical and photophysical properties. BHQ protected compounds were found to be sensitive to both one-photon excitation and two-photon excitation processes. The one-photon quantum efficiencies were found to be 0.29-0.39 upon irradiation with 365 nm UV light. The two-photon uncaging action cross-sections were determined to be 0.43-0.90 GM upon irradiation with 740 nm IR laser light. The dark hydrolysis rates of BHQ-caged compounds under simulated physiological conditions were found to be 69-105 hr. Stern-Volmer quenching experiments, a photolysis in oxygen-18 labeled water, NMR observation of BHQ-OAc photolysis in acetonitrile-$d_3$, and time-resolved spectroscopic studies were executed to understand the photolysis mechanism of BHQ, which is proposed to be a solvent assisted heterolysis mechanism involving a short-lived triplet state.

Caged ATP

ATP plays a central role in signal propagation in the nervous system. The most abundant cell type in the brain, astrocytes are a subtype of glial cells important for signaling, for which they use ATP. These cells express two different kinds of purinergic receptors: ionotropic (P2X) and metabotropic ATP receptors (P2Y). ATP binding to P2Y receptors causes an increase in intracellular inositol 1,4,5-triphosphate ($IP_3$), which signals the release of $Ca^{2+}$ from internal stores. This $Ca^{2+}$ release can be observed electrophysiologically or with $Ca^{2+}$-sensitive fluorescent indicators. Caged ATP has frequently been used to study ATP dynamics in biological systems.

ATP can be biologically inactivated through esterification of the terminal phosphate with a photoremovable protecting group. There are many caged versions of ATP, including NB-ATP (Kaplan et al., (1978) *Biochemistry* 17: 1929-1935), NPE-ATP (Walker et al., (1988) *J. Am. Chem. Soc.* 110: 7170-7177.), and DMNPE-ATP (Wootton & Trentham, (1989) *Photochemical Probes in Biochemistry*, Nielsen, P. E., Ed.; Kluwer Academic Publishers: p 277-296). The latter two are available commercially. Nevertheless, NB- and NPE-ATP have excitation wavelengths <300 nm, which are detrimental to biological preparations, and release kinetics slower than the signal transduction pathways activated by ATP. The $\lambda_{max}$ of DMNPE-ATP is in a more suitable range for physiological use (350 nm), but it is also a nitrobenzyl ester and like the others suffers from slow release kinetics. More recently, pHP-ATP and DMACM-ATP have emerged, but pHP-ATP has a low extinction coefficient at >360 nm, which enables only a small increase in ATP concentration upon irradiation. None of the existing caged ATP have sensitivity to 2PE sufficient for biological use. Other amino-coumarins have shown sensitivity to 2PE. DMACM-ATP may be released upon 2PE, but this has not been reported. The chemical quantum yield for DMACM-ATP is low yet it is fluorescent, which interferes with fluorescent sensors used in biological experiments. A BHQ-caged ATP such as described in the present disclosure provides a large quantum efficiency at wavelengths not detrimental to biological preparations (>365 nm), it is relatively non-fluorescent and highly water soluble, and it has good sensitivity to 2PE.

The compounds of the disclosure can be synthesized from BHQ with all of the steps proceeding in high yield, except for the last coupling reaction of BHQ-phosphate and ADP. The coupling step of the reaction route requires vigorously dry conditions, and other by-products (mainly polyphosphates) may be formed. The purification of BHQ-ATP (159) can be achieved by passing the crude reaction mixture through a DEAE cellulose column, collecting fractions, and further purifying by HPLC.

Figure 5:
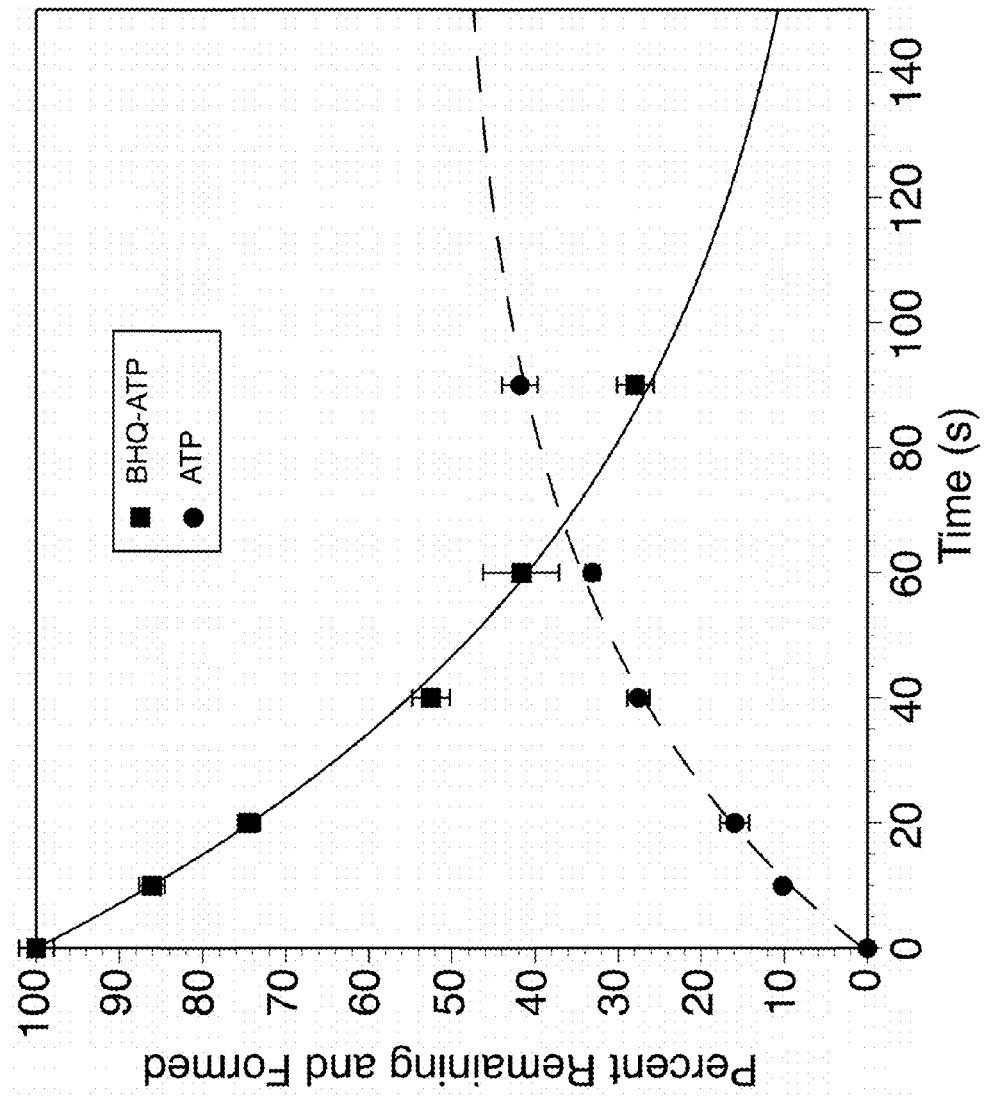
FIG. 5 is a graph illustrating the time-course of one-photon photolysis of BHQ-ATP (159) and the corresponding generation of ATP. The percent of BHQ-ATP (159) remaining and the amount of ATP formed respectively were determined by HPLC and are the averages of three runs. Lines are fits of a single exponential decay curve or rise to maximum. Error bars represent the standard deviation of the measurements.
Figure 6:
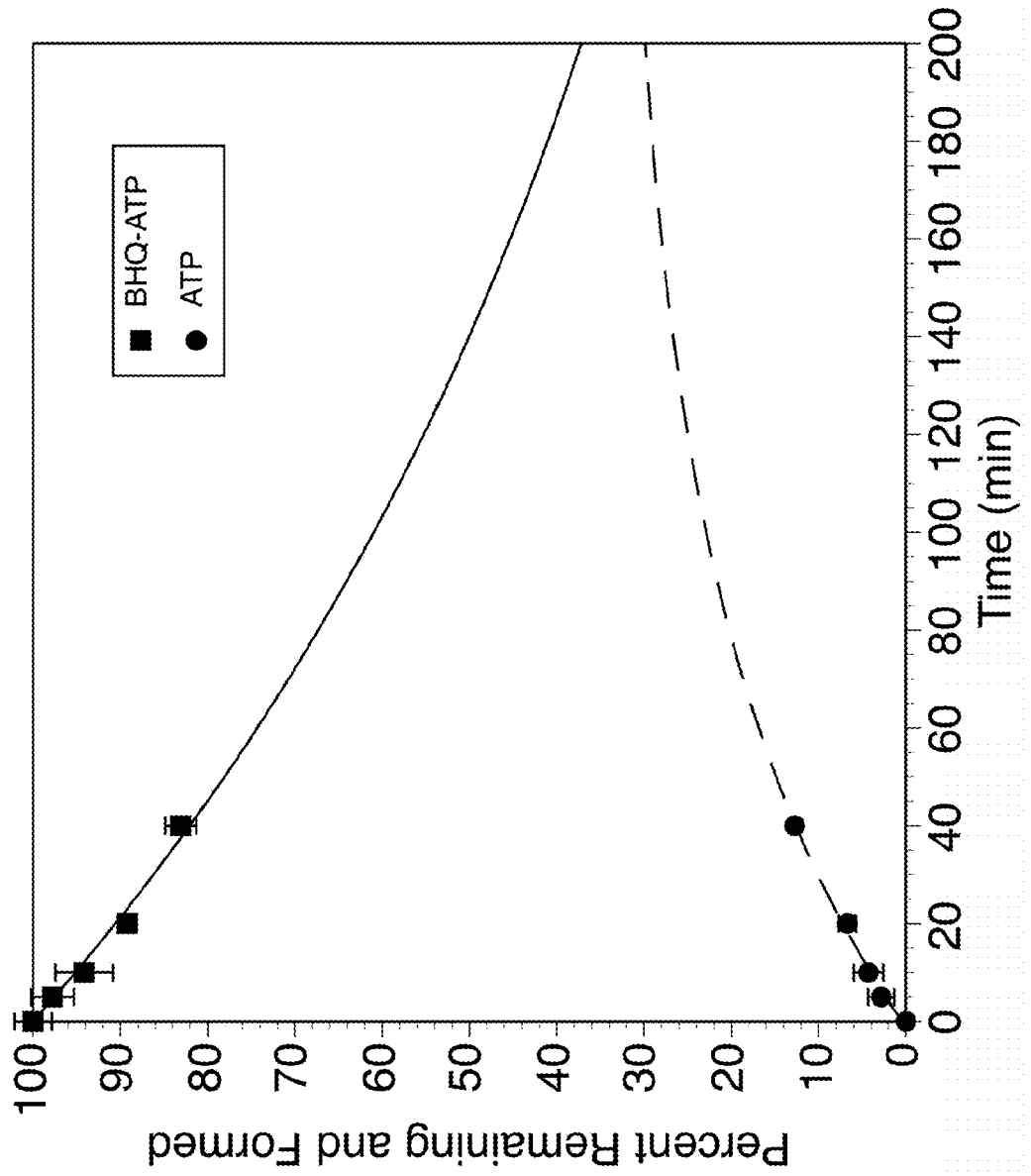
FIG. 6 is a graph illustrating the time course of two-photon photolysis of BHQ-ATP (159) and the corresponding generation of ATP. The percent of BHQ-ATP (159) remaining and the amount of ATP formed respectively were determined by HPLC and are the averages of three runs. Lines are fits of a single exponential decay curve or rise to maximum. Error bars represent the standard deviations of the measurements.

Like other BHQ caged compounds, BHQ-ATP (159) has good sensitivity, $Q_u \times \epsilon$, to one-photon excitation (228 at 365 nm), and ATP can be recovered in 70% yield. BHQ-ATP (159) also has a two-photon uncaging action cross-section of 0.17 GM, which is higher than the lower limit for two-photon excitation sensitive compounds to be useful in biological studies. Upon irradiation with a high-intensity infra-red laser, therefore, BHQ-ATP (159) can be photolyzed efficiently and ATP concentration will be raised quickly in the focal volume of the laser, as shown in FIGS. 5 and 6, for example. Possessing the good sensitivity to both one-photon and two-photon processes, decent recovery of ATP, and easy synthetic route, BHQ-ATP (159) may be used as a tool for biological and physiological studies.

It is contemplated that the methods of the present disclosure may be modified to provide various caged nucleoside phosphoesters including, but not limited to, BHQ-ATP (159). For example only, and not intended to be limiting, it is considered within the scope of the present disclosure for there to be variation in the structure of the gating, or blocking, group coupled to the selected nucleoside phosphoester. Thus, suitable gating moieties include, but are not limited to, such as 8-bromo-7-hydroxyquinoline (BHQ) (4), 8-nitro-7-hydroxyquinoline (NHQ) (5a), 8-cyano-7-hydroxyquinoline (CNQ) (5b), 8-chloro-7-hydroxyquinoline (CHQ) (5c), 7-dimethylaminoquinoline (DMAQ) (13a), 7-dimethylamino-4-chloroquinoline (DMAQ-Cl) (13b), and the like, including compounds presented in Examples 1-50 below. Various methods for the synthesis of the gating moieties of the disclosure are illustrated in Examples 1-50, below.

Figure 2:
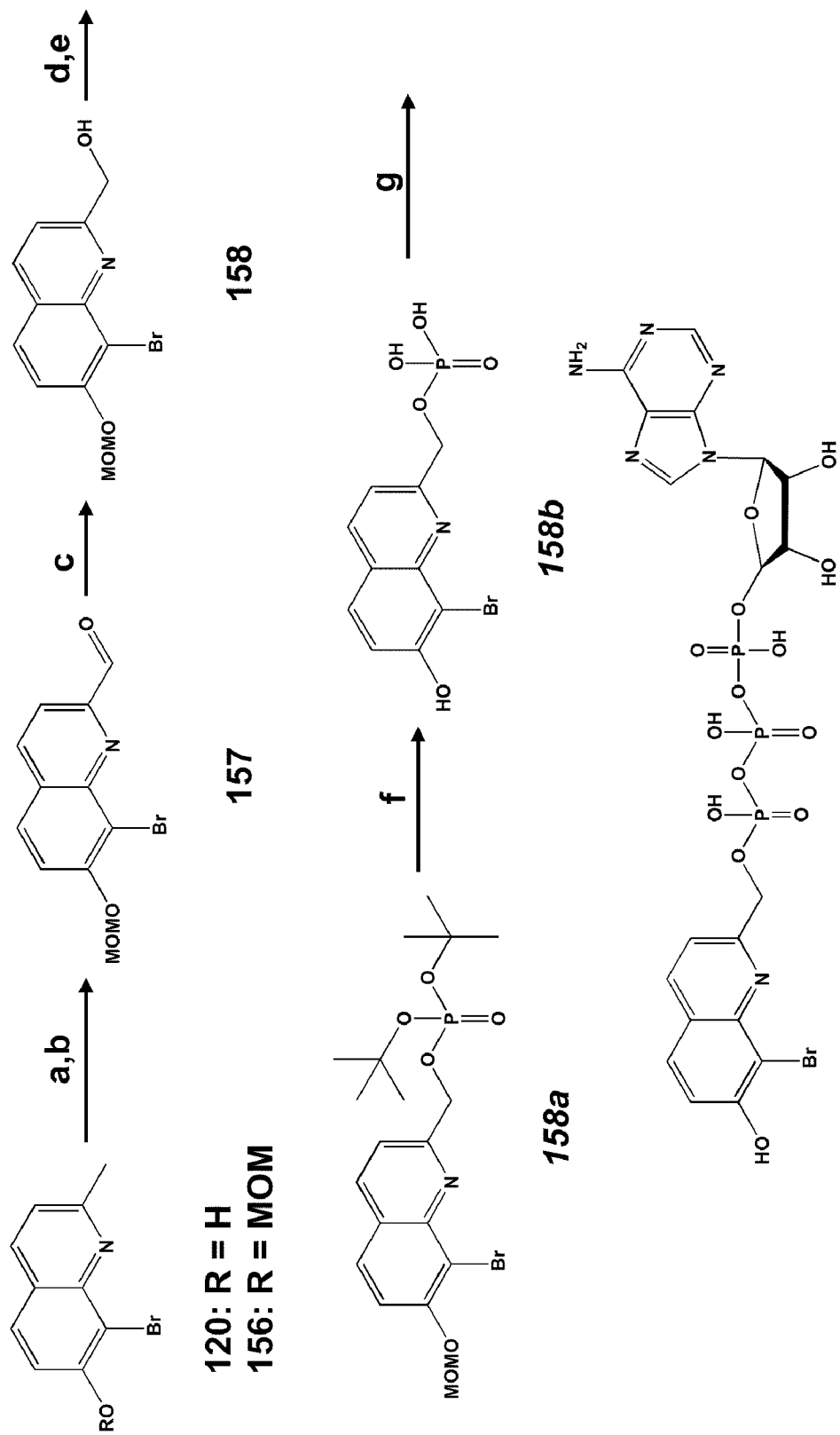
FIG. 2 schematically shows the route of synthesis of compound BHQ-ATP (159). Reagents and conditions are: (a) MOMCl, Et$_3$N, THF, room temperature, 84%; (b) SeO$_2$. p-dioxane, 80° C., 4 hr, 78%; (c) NaBH4, EtOH, room temperature, 2 hr, 94%; (d) (t-BuO)$_2$PNEt$_2$, tetrazole, THF; (e) t-BuOOH, Et$_3$N, 4 hr, 79%; (f) TFA, CH$_2$Cl$_2$, room temperature, overnight, 82%; (g) ADP, Im$_2$CO, HMPA, room temperature.

It is also within the scope of the disclosure for the compounds to further comprise a nucleoside phosphoester, including, but not limited to, adenosine monophosphate (AMP), adenosine diphosphate (ADP), adenosine triphosphate (ATP), cytosine monophosphate (CMP), cytosine diphosphate (CDP), cytosine triphosphate (CTP), guanine monophosphate (GMP), guanine diphosphate (GDP), guanine triphosphate (GTP), thymidine monophosphate (TMP), thymidine diphosphate (TDP), and thymidine triphosphate (TTP), or derivatives and analogs thereof. The synthesis of a conjugate between ATP and BHQ to provide BHQ-ATP (159) is shown in FIG. 2, and described in Example 6 below.

One aspect of the disclosure, therefore, encompasses caged compounds having the formula:

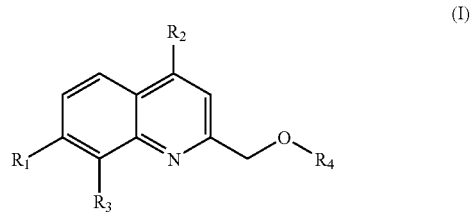

(I)

where $R_1$ can be selected from the group consisting of: HO—, HS—, and (Me)$_2$N—; $R_2$ can be selected from the group consisting of: H and Cl; $R_3$ can be selected from the group consisting of: H, NO$_2$, CN, Cl, and Br; and $R_4$ can be selected from the group consisting of: acetyl- and a nucleoside phosphoester.

In these embodiments, the caged compound can have the characteristic that upon excitation with two photon laser excitation light energy the caged compound becomes uncaged.

In embodiments of this aspect of the disclosure, the nucleoside phosphoester can be selected from the group consisting of: adenosine monophosphate (AMP), adenosine diphosphate (ADP), adenosine triphosphate (ATP), cytosine monophosphate (CMP), cytosine diphosphate (CDP), cytosine triphosphate (CTP), guanine monophosphate (GMP), guanine diphosphate (GDP), guanine triphosphate (GTP), thymidine monophosphate (TMP), thymidine diphosphate (TDP), and thymidine triphosphate (TTP).

In some embodiments of this aspect of the disclosure, the caged compounds may have the formula:

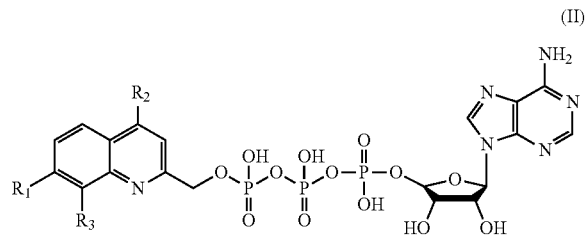

(II)

where $R_1$ is selected from the group consisting of: HO, HS, and (Me)$_2$N; $R_2$ is selected from the group consisting of: H and Cl; and $R_3$ is selected from the group consisting of: H, NO$_2$, and Br.

In one embodiment of this aspect of the disclosure, the caged compound can have the formula:

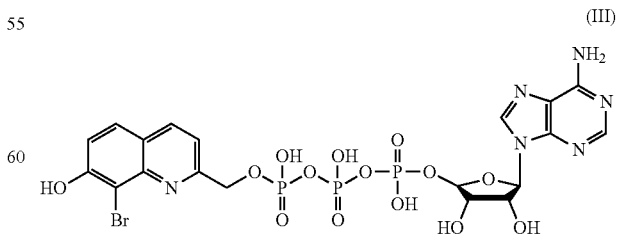

(III)

Another aspect of the disclosure provides methods of synthesizing a caged nucleoside, comprising: (a) protecting the free hydroxy group of BHQ with a protecting group; (b)

synthesizing a protected BHQ-alcohol; (c) synthesizing a protected BHQ-phosphate from the protected BHQ-alcohol, wherein the phosphate has protecting groups thereon; (d) removing the protecting groups from the protected BHQ-phosphate; (e) coupling of the BHQ-phosphate and an activated nucleotide; and (f) isolating a BHQ-nucleotide.

In one embodiment of the methods of this aspect of the disclosure, the activated ADP can be ADP-imidazolide and the BHQ-nucleotide can be BHQ-ATP (III).

Yet another aspect of the disclosure provides for methods of detecting a biochemical or physiological reaction in a biological sample, comprising the steps of: (a) obtaining a biological sample; delivering to the biological sample a caged compound; (c) irradiating the biological sample with light energy, thereby dissociating the caged nucleotide to provide an uncaged nucleotide and initiating a biochemical or physiological reaction in the biological sample; and (d) detecting the detecting the biochemical or physiological reaction in the biological sample.

In embodiments of this aspect of the disclosure, the methods may further comprise the steps of: (i) contacting the biological sample with an indicator composition, wherein the indicator composition responds to the biochemical or physiological reaction by providing a detectable signal; (ii) allowing the indicator composition to emit a detectable signal; and (iii) detecting the emitted signal, thereby detecting the biochemical or physiological reaction.

In other methods of this aspect of the disclosure, the physiological reaction can generate an electrophysiological signal, and the method may further comprise the step of detecting the electrophysiological signal.

In embodiments of the methods of this aspect of the disclosure, the biological sample can be selected from the group consisting of: an animal or a human subject, an isolated tissue sample, an isolated cell or population of cells, a cultured cell population, and a biological fluid.

In some embodiments of this aspect of the disclosure, the indicator composition can provide a detectable signal in response to the generation of a metabolite, wherein the generation of the metabolite can be initiated by the uncaging of a caged nucleotide.

In some embodiments, the metabolite can be selected from a metal ion, a nucleotide, and a compound transformed by the release of the uncaged compound.

In one embodiment of the methods of the disclosure, the metabolite is a calcium ion.

In embodiments of this aspect of the disclosure, the caged compound can have a structure according to the formula:

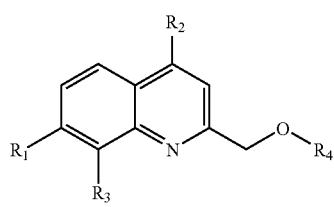

(I)

where $R_1$ is selected from the group consisting of: HO—, HS—, and $(Me)_2N$—; $R_2$ is selected from the group consisting of: H and Cl; $R_3$ is selected from the group consisting of: H, $NO_2$, CN, Cl, and Br; and $R_4$ is selected from the group consisting of: acetyl- and a nucleoside phosphoester, and wherein the nucleoside phosphoester is selected from the group consisting of: adenosine monophosphate (AMP), adenosine diphosphate (ADP), adenosine triphosphate (ATP), cytosine monophosphate (CMP), cytosine diphosphate (CDP), cytosine triphosphate (CTP), guanine monophosphate (GMP), guanine diphosphate (GDP), guanine triphosphate (GTP), thymidine monophosphate (TMP), thymidine diphosphate (TDP), and thymidine triphosphate (TTP).

In some embodiments of this aspect of the disclosure, the caged nucleotide can have the structure according to the formula:

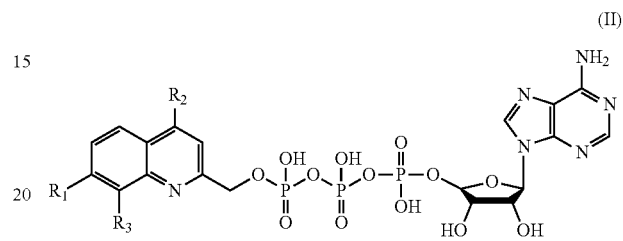

(II)

where $R_1$ is selected from the group consisting of: HO, HS, and $(Me)_2N$; $R_2$ is selected from the group consisting of: H and Cl; and $R_3$ is selected from the group consisting of: H, $NO_2$, and Br.

In embodiments of this aspect of the disclosure, the caged compound can be selected from the group consisting of: BHQ-ATP, BHQ-OAc, NHQ-OAc, CyHQ-OAc, CHQ-OAc, DMAQ-OAc, DMAQ-Cl-OAc, and TQ-OAc.

In one embodiment of the methods of the disclosure, the caged nucleotide is BHQ-ATP having the structure according to the formula:

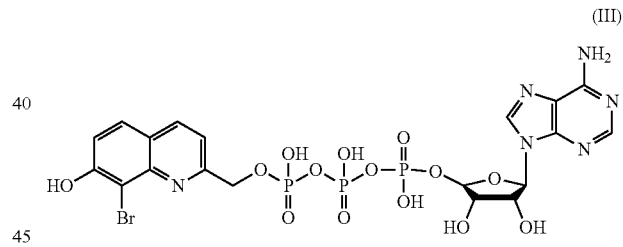

(III)

In another embodiment of this aspect of the disclosure, the light energy irradiating the biological sample comprises a first laser light having a first wavelength and a second laser light having a second wavelength, thereby uncaging a target caged compound by two photon laser excitation (2PE).

In one embodiment, the indicator composition emits a detectable signal in response to $Ca^{2+}$.

In some embodiments of the methods of this aspect of the disclosure, the caged compound can be delivered to the biological sample as a pharmaceutically acceptable composition, where the pharmaceutically acceptable composition can comprise the gated compound and a pharmaceutically acceptable carrier.

Still another aspect of the disclosure is a composition comprising a caged compound according to any of the embodiments described above, and a pharmaceutically acceptable carrier.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, +5%, ±6%, ±7%, ±8%, ±9%, or ±10%, or more of the numerical value(s) being modified.

EXAMPLES

Example 1

Synthesis of BHQ-ATP (159)

The synthesis of BHQ-ATP (159) (shown in FIG. 1) started from BHQ (120) in seven steps as schematically shown in FIG. 2. BHQ was treated with triethylamine and chloromethyl methyl ether in THF to protect the free hydroxy group. The next step was a selenium dioxide oxidation, which required the free hydroxy on quinoline to be protected. The methoxymethyl (MOM) protecting group is preferred because it is stable to the oxidation conditions and it is removed a few steps later with the deprotection of the phosphate. The aldehyde (157) was prepared, and then reduced with sodium borohydride to the alcohol (158). Compound (158) was then converted to phosphate using phosphoramidite chemistry. Treating (158) with tetrazole, and di-tert-butyl-N,N-diethylphosphoramidite in THF generated BHQ-phosphite, which was oxidized with tert-butyl hydroperoxide to yield phosphate (158a) in 79% for 2 steps. The MOM-protected BHQ-phosphate (158a) was treated with TFA in dichloromethane and stirred overnight to yield BHQ-phosphate (158b) in 85% yield. Both the MOM protecting group and the two tert-butyl group on the phosphate were removed. BHQ-ATP (159) was synthesized from the coupling of BHQ-phosphate (158b) and activated ADP under vigorously anhydrous conditions. The BHQ-phosphate and ADP were dried by sequential cycles of dissolution and evaporation in pyridine and DMF. Tri-n-octylamine and tri-n-butylamine were used to cap the hydroxy groups on the phosphates away from the expected reaction site. Tri-n-octylamine (1 eq) was used to transform BHQ-phosphate to its tri-octylammonium salt, and tri-n-butylamine (2 eq) was used to change ADP to its tri-butylammonium salt. The ADP salt was activated by treatment with carbonyldiimidazole to form ADP imidazolide in DMF and dried. The BHQ-phosphate salt was mixed with the activated ADP imidazolide in HMPA and stirred for two days.

The purification of BHQ-ATP (159) was performed with a DEAE cellulose column using a step gradient elution of aqueous ammonium bicarbonate. The ammonium salt of BHQ-ATP (159) was acquired and further purified on a reverse phase C18 HPLC column using a methanol/water solvent system. The molecular structure was confirmed by $^1$H NMR, $^{31}$P NMR, and HRMS.

Example 2

UV Absorption of BHQ-ATP (159)

Figure 3:
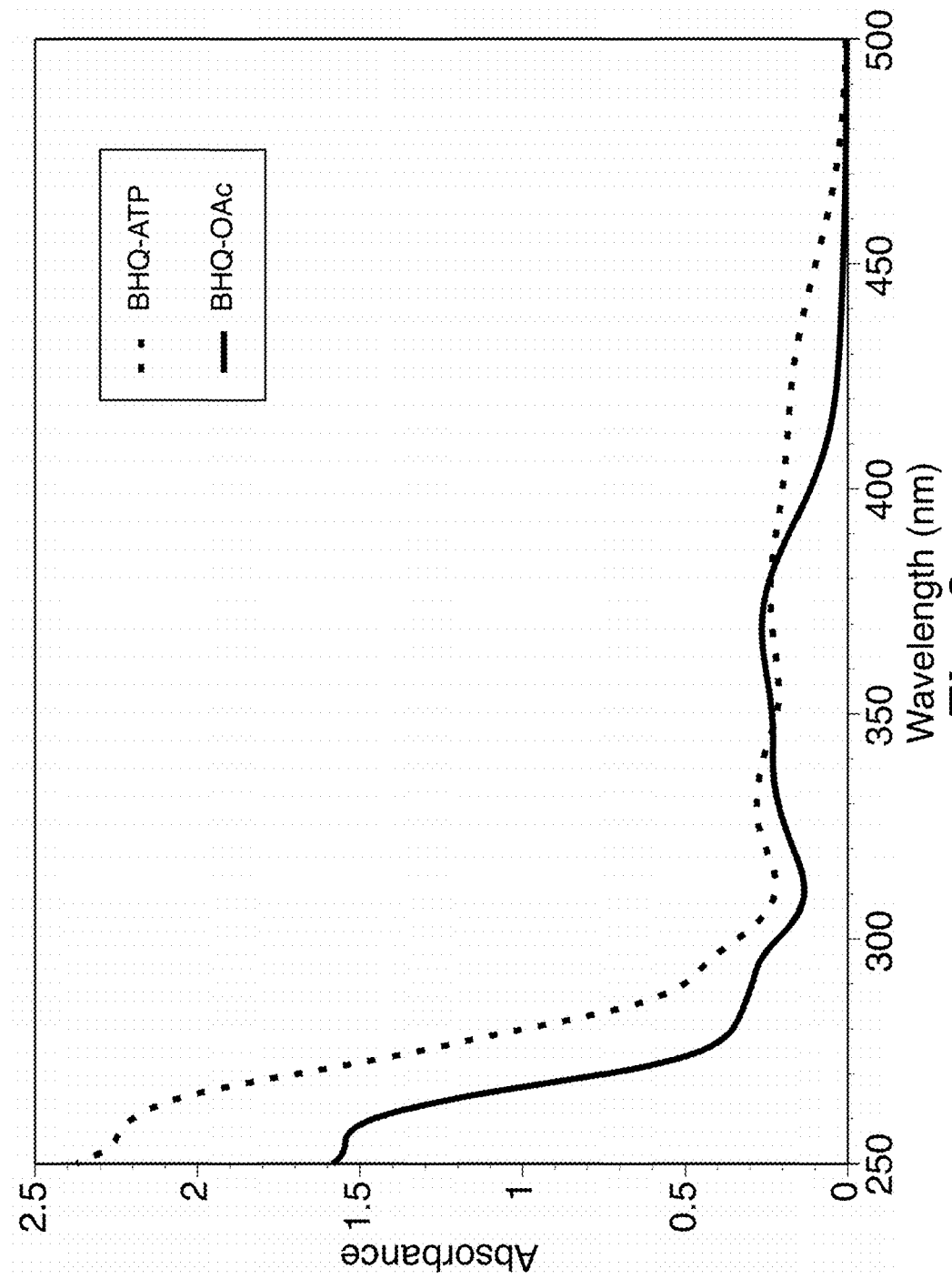
FIG. 3 is a graph comparing the UV and visible absorption spectra of BHQ-ATP (159) and BHQ-OAc (157).

The UV absorption spectra of BHQ-ATP (159) in KMOPS buffer is similar to that of BHQ-OAc, as shown in FIG. 3. It has two absorptive bands beyond 300 nm, one at 320 nm and the other at 370 nm. The 370 nm absorption band arises from the phenolate form of the BHQ skeleton, and the 320 nm absorption band is from the phenol form. In contrast with the UV absorption spectrum of BHQ-OAc, the BHQ-ATP (159) absorbed more at 320 nm than 370 nm, which indicated that in KMOPS buffer, the phenolic form of BHQ-ATP (159) predominated over the phenolate form. The $\lambda_{max}$ of BHQ-ATP (159) is 376 nm, and the extinction coefficient at this wavelength is 1300 M$^{-1}$cm$^{-1}$.

Example 3

Photolysis of BHQ-ATP (159)

Figure 4:
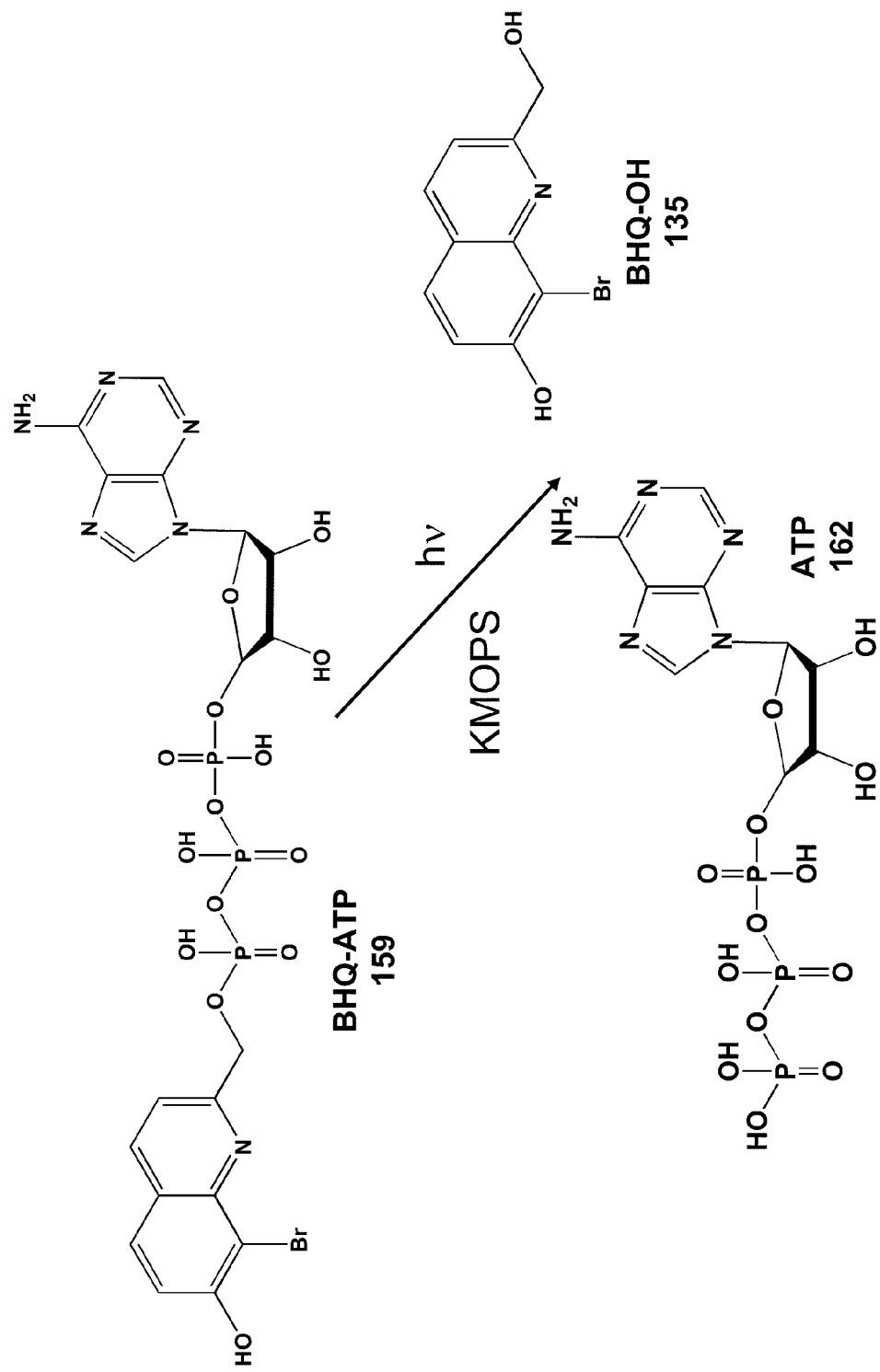
FIG. 4 schematically illustrates the photolysis of BHQ-ATP (159).

The quantum efficiency of BHQ-ATP (159) decay and ATP recovery were determined by photolyzing a KMOPS solution of BHQ-ATP (159) (100 μM) with light from a 365 nm lamp through a set of filters that narrowed the band of light to a tight 30 nm range around 365 nm. The photolytic reactions are schematically shown in FIG. 4. Aliquots (20 μL) were taken out from the photolysis cuvette after a time interval of 0, 10, 20, 40, 60, or 90 secs, and HPLC analyses of these samples with a reverse phase C18 column and 85% 25 mM KH$_2$PO$_4$ buffer (pH=6.2)/15% methanol solvent system were carried out. The BHQ-ATP (159) peak (retention time=4.2 min.) and ATP peak (retention time=2.8 min.) were recorded and analyzed. The decay of BHQ-ATP (159) and the rise of ATP could be fit to single exponential curves as shown in FIG. 5.

The one-photon quantum efficiency was 0.19, which is similar to the values measured for other BHQ caged compounds. The yield of ATP was about 70%. BHQ-ATP (159) is extremely stable in the dark under simulated physiological conditions (KMOPS, pH=7.2). The time constant for dark hydrolysis was about 1000 hr. In a separate experiment, an NMR sample of BHQ-ATP (159) in D$_2$O was stable over the course of 2 weeks.

Knowing that BHQ-ATP (159) can be photolyzed efficiently and possesses a decent yield of ATP upon irradiation with UV light, the two-photon photolysis of BHQ-ATP (159) was also performed and monitored by HPLC to determine the two-photon uncaging action cross-section. BHQ-ATP (159) (100 μM in KMOPS, pH=7.2) was photolyzed with a Chameleon Ultra II laser at 740 nm in 25-μL aliquots. The irradiation time intervals of the pulsed laser were 0, 5, 10, 20, and 40 min. Three samples of each time interval were collected and analyzed by HPLC using the same method as in the one-photon photolysis. The decay of BHQ-ATP (159) and rise of ATP could be fit to single exponential curves as shown in FIG. 6. Using Tsien's method of determining two-photon uncaging action cross-section with a fluorescence reference solution, the two-photon uncaging action cross-section of BHQ-ATP (159) was measured to be 0.17 GM. The ATP yield was about 40%.

Example 4

MOM-BHQ (156)

Referring to FIG. 2, BHQ 120 (1.83 g, 7.38 mmol) was dissolved in THF (30 mL). Triethylamine (2.00 mL, 14.2 mmol) was added to the solution. After 2 min of stirring, chloromethyl methyl ether (1.00 mL, 13.2 mmol) was added dropwise and the reaction was stirred overnight. The solvents were evaporated, and the residue dissolved with chloroform (100 mL). The chloroform solution was washed with water and brine, and dried over anhydrous $Na_2SO_4$. The solvent was evaporated and the residue was purified by flash chromatography with EtOAC/hexane (1:9) to yield 156 (1.74 g, 6.17 mmol, 84% yield).

$^1$H NMR ($CDCl_3$) δ 7.98 (1H, d, J=8.0 Hz), 7.70 (1H, d, J=9.2 Hz), 7.43 (1H, d, J=9.2 Hz), 7.24 (1H, d, J=8.0 Hz), 5.40 (2H, s), 3.58 (3H, s), 2.80 (3H, s); $^{13}$C NMR ($CDCl_3$) δ 161.08, 155.11, 146.30, 136.48, 127.97, 123.64, 121.32, 116.57, 112.14, 95.63, 56.84, 26.05; FTIR (neat) 2906, 2844, 1614, 1508, 1322, 1248, 1154, 1056, 993, 920, 831 cm$^{-1}$; HR-MS (ESI) m/z calculated for $(C_{12}H_{12}BrNO_2+H)^+$ 282.0130 ($^{79}$Br) and 284.0109 ($^{81}$Br), found 282.0132 ($^{79}$Br) and 284.0107 ($^{81}$Br).

Example 5

MOM-BHQ Aldehyde (157)

Referring to FIG. 2, MOM-protected BHQ 156 (250 mg, 0.887 mmol) was dissolved in p-dioxane (5 mL). Selenium dioxide (100 mg, 0.901 mmol) was added to the solution, and the mixture was heated at 80° C. for 4 h with stirring. The reaction mixture was vacuum filtered and the filtrate was concentrated. The remaining residue was purified by flash chromatography using EtOAc/hexane (1:3) to provide 157 (205 mg, 0.693 mmol, 78% yield).

$^1$H NMR ($CDCl_3$) δ 10.30 (1H, s), 8.27 (1H, d, J=8.4 Hz), 7.97 (1H, d, J=8.4 Hz), 7.84 (1H, d, J=9.2 Hz), 7.66 (1H, d, J=9.6 Hz), 5.45 (2H, s), 3.60 (3H, s); $^{13}$C NMR ($CDCl_3$) δ 193.86, 156.05, 153.58, 146.49, 137.98, 128.20, 127.16, 119.94, 116.47, 113.29, 95.60, 56.97; FTIR (neat) 2933, 2834, 1708, 1615, 1442, 1261, 1156, 1038, 920, 839 cm$^{-1}$; HR-MS (ESI) m/z calculated for $(C_{12}H_{10}BrNO_3+H)^+$ 295.9922 ($^{79}$Br) and 297.9902 ($^{81}$Br), found 295.9925 ($^{79}$Br) and 297.9895 ($^{81}$Br).

Example 6

MOM-BHQ Alcohol (158)

Referring to FIG. 2, MOM-protected BHQ aldehyde 157 (150 mg, 0.51 mmol) was mixed with ethanol, then sodium borohydride (15 mg, 0.41 mmol) was added in small portions to the mixture. When the reaction was complete as determined by TLC, it was concentrated, and the remaining residue was diluted with chloroform. The mixture was then washed successively with water and brine, dried over anhydrous $Na_2SO_4$, and evaporated to provide 158 (140 mg, 0.47 mmol, 92%).

$^1$H NMR ($CDCl_3$) δ 8.08 (1H, d, J=8.4 Hz), 7.76 (1H, d, J=8.8 Hz), 7.50 (1H, d, J=8.8 Hz), 7.22 (1H, d, J=8.4 Hz), 5.42 (2H, s), 4.94 (2H, s), 3.58 (3H, s); $^{13}$C NMR ($CDCl_3$) δ 160.45, 155.58, 144.96, 137.24, 128.05, 124.54, 117.39, 117.11, 112.12, 95.58, 64.26, 56.88; FTIR (neat) 3294, 2935, 1618, 1514, 1256, 1197, 1152, 1055, 989, 916, 835 cm$^{-1}$; HR-MS (ESI) m/z calculated for $(C_{12}H_{12}BrNO_3+H)^+$ 298.0079 ($^{79}$Br) and 300.0058 ($^{81}$Br), found 298.0075 ($^{79}$Br) and 300.0056 ($^{81}$Br).

Example 7

MOM-BHQ di-tert-butyl phosphate (158a)

Figure 7:
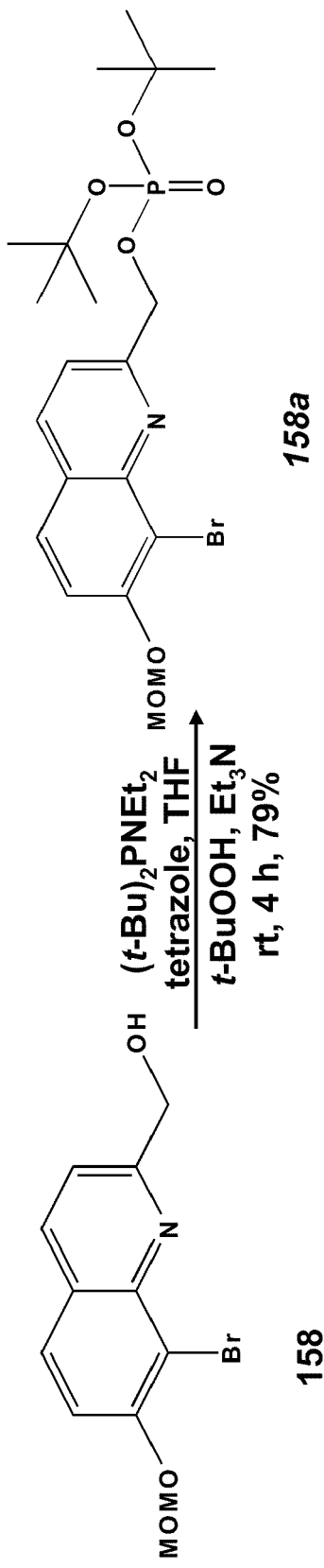
FIG. 7 schematically illustrates the synthesis of the intermediate MOM-BHQ di-tert-butyl phosphate (158a).
Figure 8:
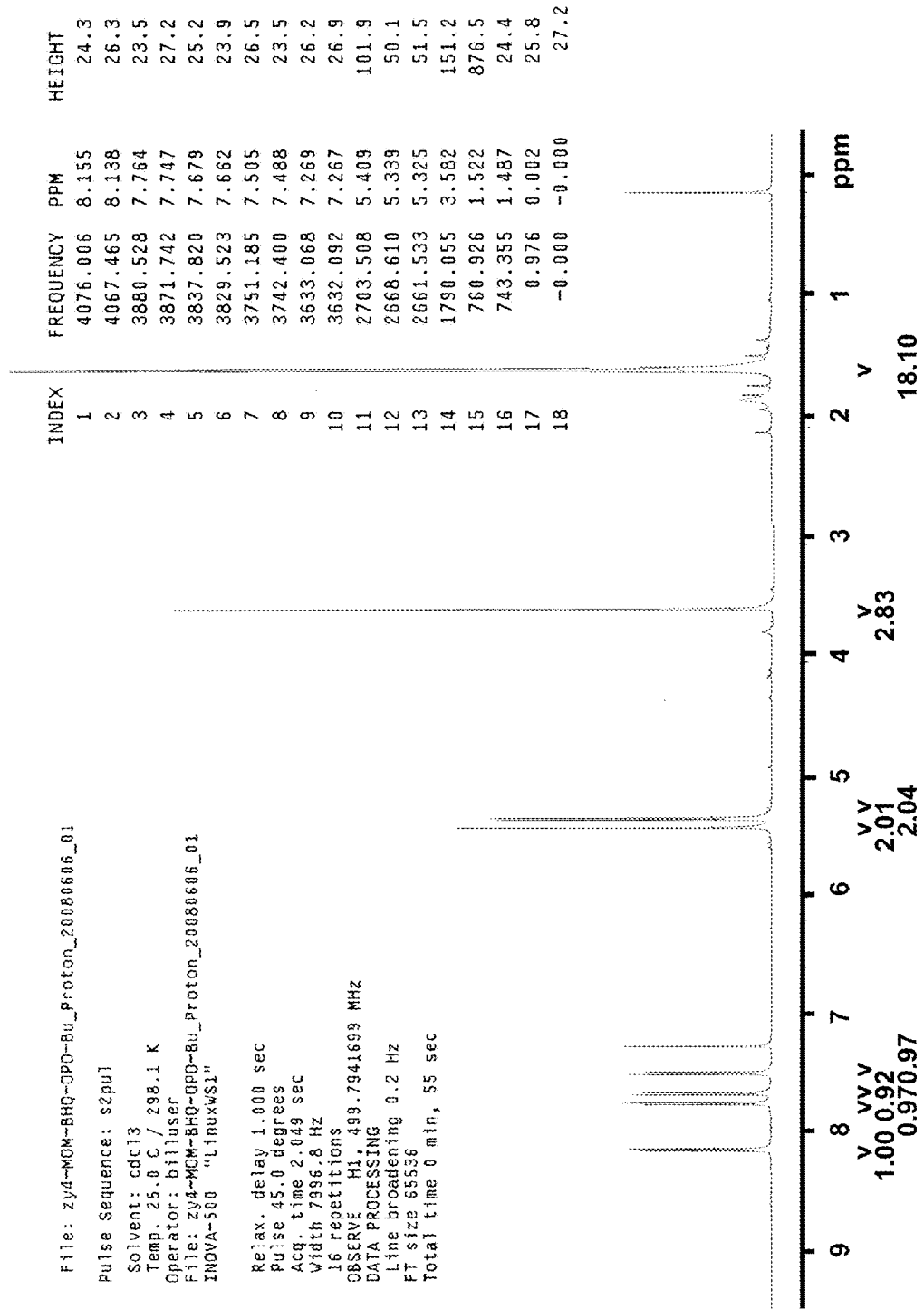
FIG. 8 shows results of an NMR analysis of MOM-BHQ di-tert-butyl phosphate (158a).

Referring to FIG. 2, MOM-protected BHQ alcohol 158 (450 mg, 1.51 mmol) was dissolved in THF (10 mL). Tetrazole (0.45 M solution in acetonitrile, 13.5 mL, 6.08 mmol) was added to the solution, and the mixture was stirred in a −20° C. bath for 5 min. Di-tert-butyl N,N-diethylphosphoramidite (0.630 mL, 2.26 mmol) was added dropwise. After 10 min of stirring at −20° C., the reaction mixture was allowed to warm to 0° C. and stirred for 1 hr. The mixture was treated with triethylamine (2.12 mL, 15.1 mmol) followed by addition of tert-butylhydroperoxide (70% in water, 1.0 mL, 7.3 mmol) at 0° C. and the mixture was allowed to warm to room temperature. After an additional 4 hr of reaction time, the excess oxidant was destroyed by addition of concentrated sodium thiosulfate solution, as schematically illustrated in FIG. 7. The mixture was concentrated, diluted with chloroform, and washed with water and brine. The organic layer was dried over $Na_2SO_4$, and concentrated. The remaining residue was purified by flash chromatography using EtOAc/Hexane (4:6) to yield (158a) (550 mg, 1.12 mmol, 79% yield), the NMR spectrum of which is shown in FIG. 8 and the FTIR spectrum is shown in FIG. 9.

$^1$H NMR: ($CDCl_3$) δ 8.15 (1H, d, J=8.4 Hz), 7.76 (1H, d, J=8.8 Hz), 7.67 (1H, d, J=8.4 Hz), 7.50 (1H, d, J=8.8 Hz), 5.41 (2H, s), 5.33 (2H, d, J=6.8 Hz), 3.58 (3H, s); $^{13}$C NMR: ($CDCl_3$) δ 159.37, 155.40, 145.83, 137.29, 128.15, 124.66, 118.13, 117.39, 112.19, 95.60, 83.06, 69.67, 56.87, 30.15; $^{31}$P NMR: ($CDCl_3$) δ-7.00; FTIR: (neat) 2985, 1618, 1512, 1375, 1261, 1158, 1046, 991, 941 cm$^{-1}$; HR-MS: (ESI) m/z calculated for $(C_{20}H_{29}BrNO_6P+H)^+$ 490.0994 ($^{79}$Br) and 492.0974 ($^{81}$Br), found 490.0997 ($^{79}$Br) and 492.0978 ($^{81}$Br).

Example 8

BHQ Phosphate (free) (158b)

Figure 10:
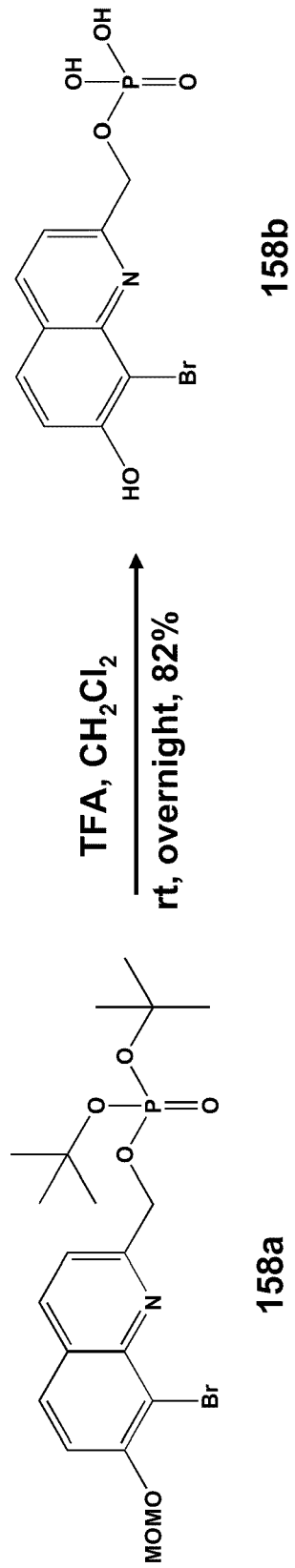
FIG. 10 schematically illustrates the formation of BHQ phosphate (158b) from MOM-BHQ di-tert-butyl phosphate (158a).
Figure 11:
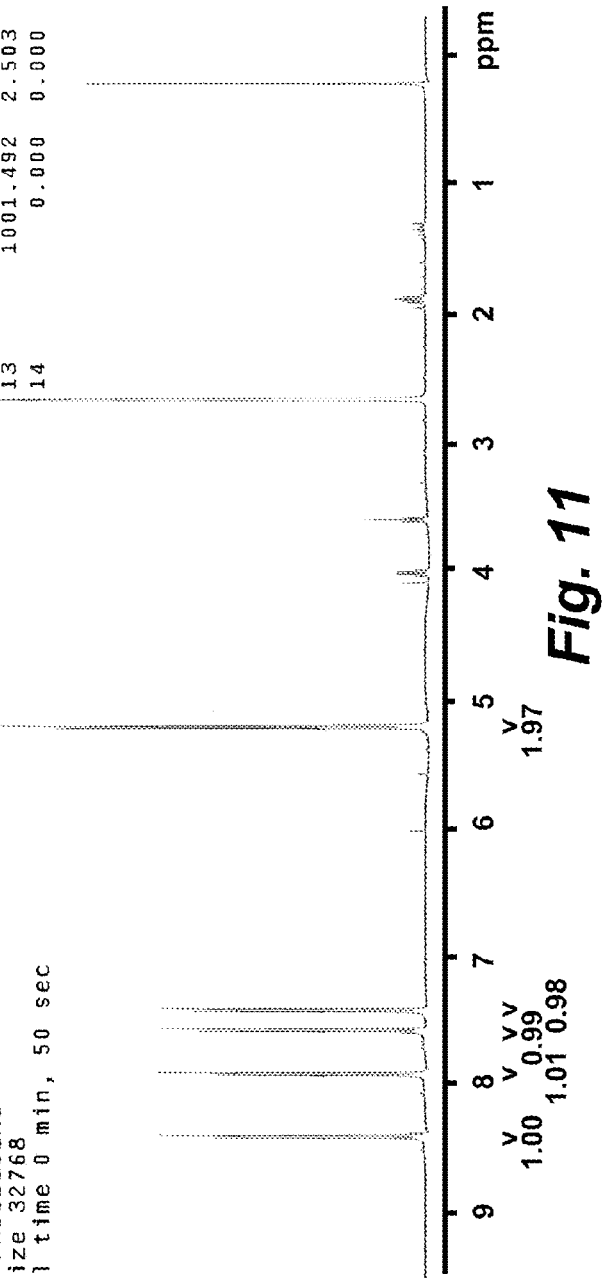
FIG. 11 shows results of an NMR analysis of BHQ phosphate (158b).
Figure 12:
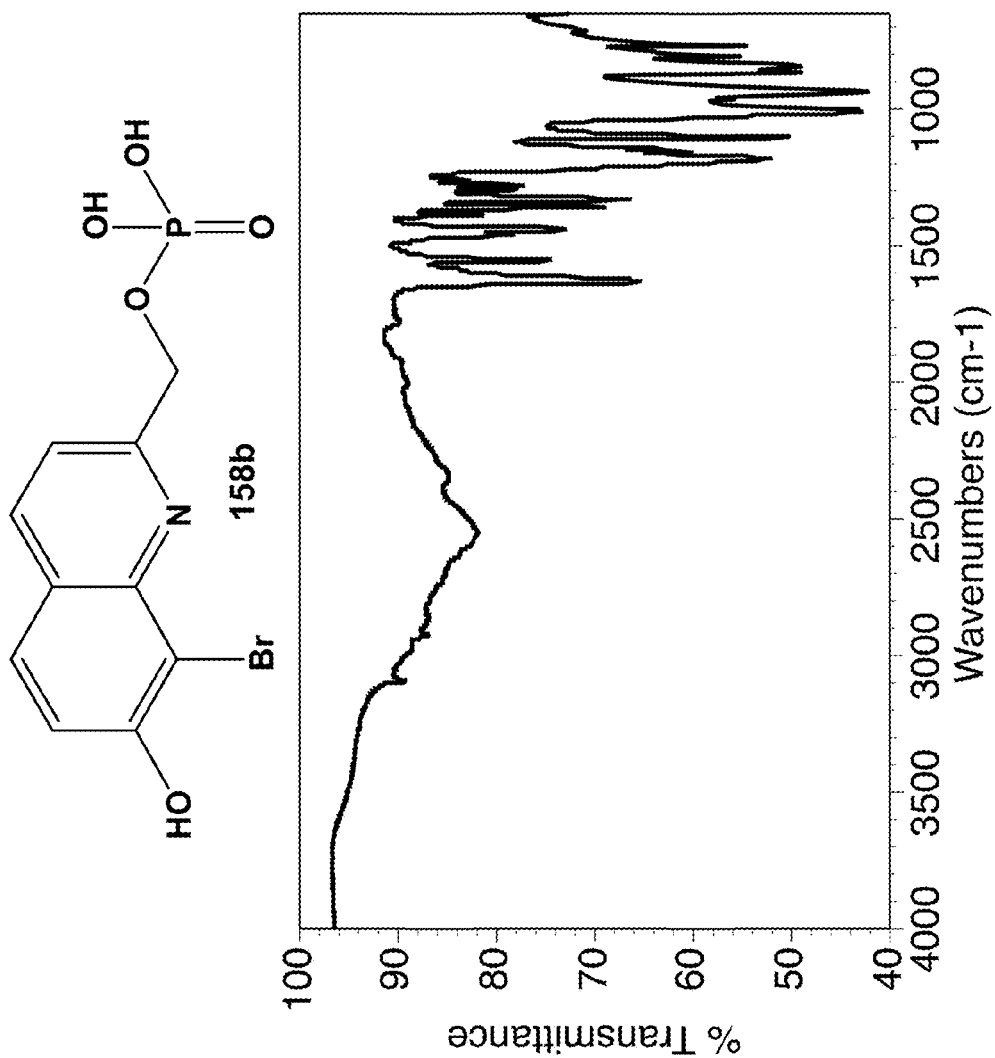
FIG. 12 is a graph showing the FTIR spectrum for BHQ phosphate (158b).

Referring to FIG. 2, MOM-protected BHQ di-tert-butyl phosphate (158a) (550 mg, 1.12 mmol) was dissolved in anhydrous dichloromethane (7 mL). Trifluoroacetic acid (0.5 mL, 6.62 mmol) was added and the resulting mixture was stirred overnight. The precipitate formed was filtered, washed with hexane (10 mL×3) and then dried under vacuum to provide (158b) (FIG. 12A) (308 mg, 0.922 mmol, 82% yield), as schematically shown in FIG. 10. The NMR spectrum of 158b is shown in FIG. 11, and the FTIR spectrum is shown in FIG. 12.

¹H NMR (DMSO-d₆) δ 8.35 (1H, d, J=8.4 Hz), 7.86 (1H, d, J=9.2 Hz), 7.51 (1H, d, J=8.4 Hz), 7.35 (1H, d, J=9.2 Hz), 5.10 (2H, d, J=8.4 Hz); ¹³C NMR (DMSO-d₆) δ 159.78, 156.93, 146.03, 138.22, 128.85, 123.67, 119.91, 117.89, 105.78, 69.23; ³¹P NMR (DMSO-d₆) δ 2.17; FTIR: (neat) 2555, 1637, 1558, 1447, 1336, 1185, 1108, 1014, 936, 866, 843 cm⁻¹; HR-MS: (ESI) m/z calculated for (C₂₀H₂₉BrNO₆P+H)⁺ 333.9480 (⁷⁹Br) and 335.9459 (⁸¹Br), found 333.9486 (⁷⁹Br) and 335.9472 (⁸¹Br).

Example 9

Synthesis of BHQ-ATP (159)

Figure 13:
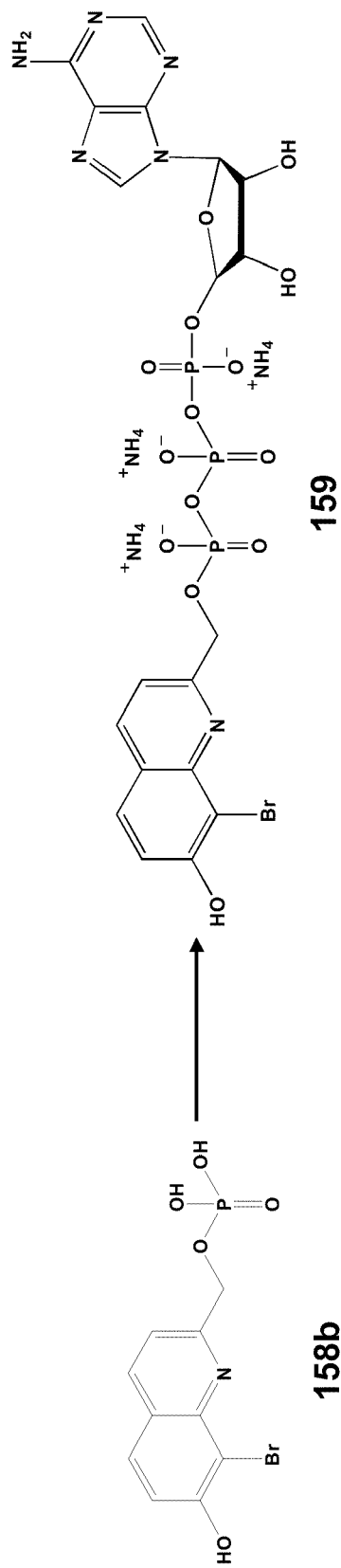
FIG. 13 schematically illustrates the addition of ADP to BHQ phosphate (158b) to form the ammonium salt of BHQ-ATP (159).
Figure 14:
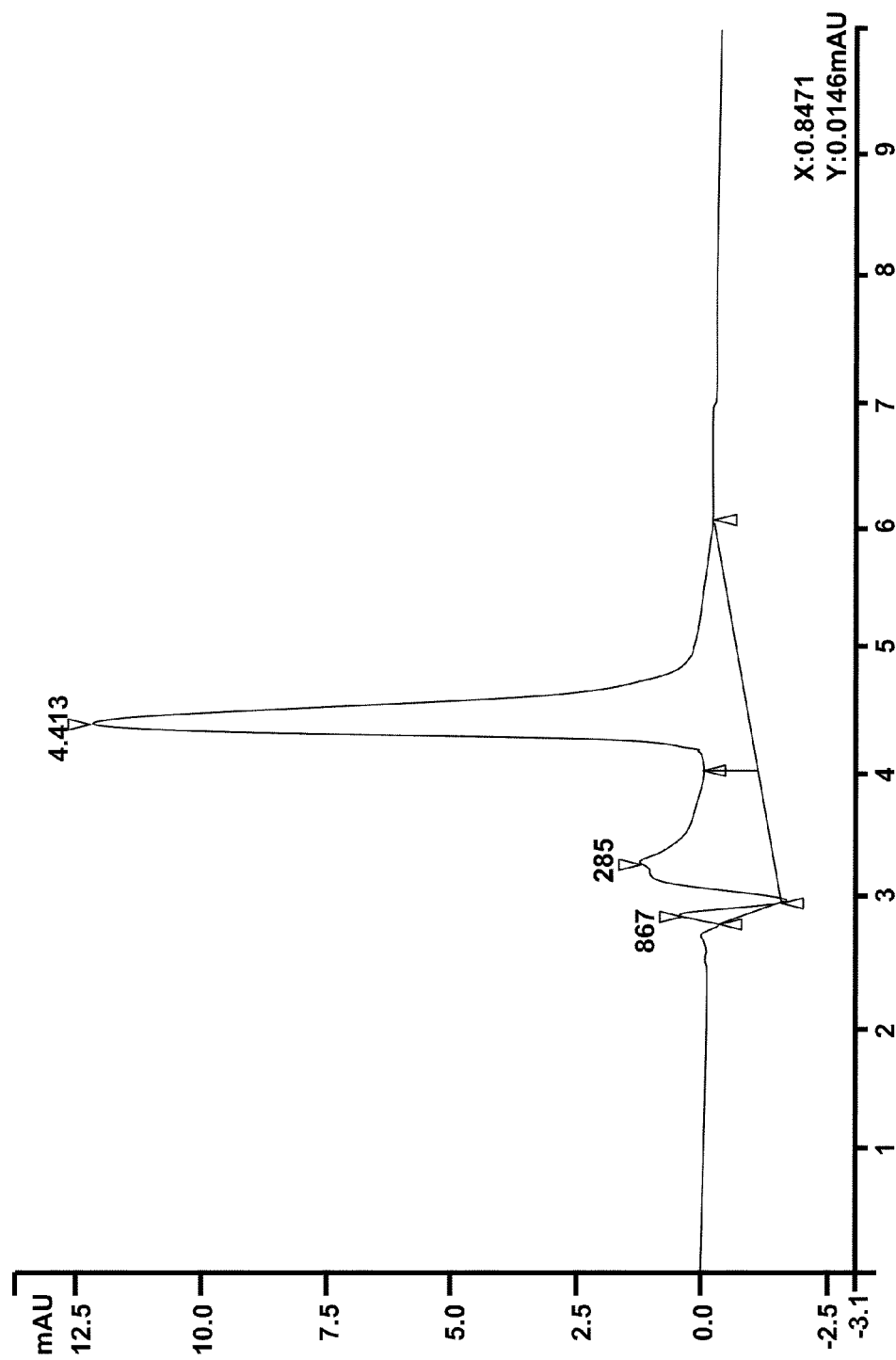
FIG. 14 is a digital image of the HPLC chromatogram for BHQ-ATP (159).
Figure 15:
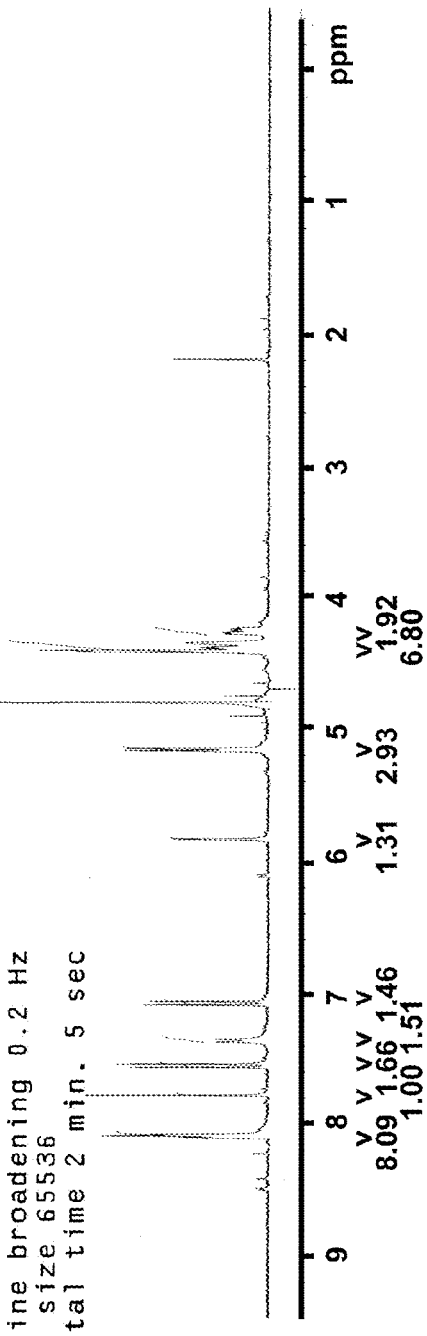
FIG. 15 is a graph that illustrates results of an NMR analysis of BHQ-ATP (159).

Referring to FIG. 2, the synthesis of BHQ-ATP (159) from (158) is schematically presented in FIG. 13. ADP (511 mg, 1.20 mmol) was dissolved in water, tri-n-butylamine (106 mg, 0.570 mL, 2.39 mmol) was added to the solution. The mixture was evaporated and the remaining residue was further dried by sequential cycles of dissolution and evaporation of dry pyridine (2 mL×2) and dry DMF (2 mL×2). The dried residue was redissolved in dry DMF (2 mL), carbonyldiimidazole (800 mg, 4.93 mmol) was added. The resulting mixture was stirred overnight under nitrogen at ambient temperature. The solvent was then evaporated. Meanwhile, BHQ phosphate (158b) was mixed with tri-n-octylamine (131 mg, 0.370 mL, 0.837 mmol) in water, followed by solvent evaporation. The remaining residue was dried by cycles of dissolution and evaporation of dry pyridine (2 mL×2) and dry DMF (2 mL×2). The resulting gummy residue was redissolved in dry DMF (2 mL) and added to the above ADP imidazole mixture. The DMF was evaporated and anhydrous HMPA (3 mL) added to the residue. The mixture was stirred for 2 days under a nitrogen atmosphere. The reaction was quenched with water (15 mL) and washed with chloroform (10 mL×4) and hexane (10 mL). The aqueous layer was poured to a DEAE-cellulose column (bicarbonate form, 50 mL dry volume). The column was eluted successively with water (100 mL), and a stepping gradient of ammonium bicarbonate solution (0.05-0.30 M, 0.05 M increments, 500 mL of each concentration). The fractions with only one component were combined and purified by HPLC (15% MeOH, 85% water, 3.3 min retention time). The pure fractions were combined and evaporated to dryness to yield 94 (90 mg, 0.11 mmole, 9.4% yield). An HPLC (85% 25 mM KH₂PO₄ buffer/15% methanol) chromatogram of BHQ-ATP (159) in KMOPS is shown in FIG. 14, the NMR spectrum is shown in FIG. 15, and the FTIR spectrum is shown in FIG. 16.

¹H NMR: (D₂O) δ 7.91 (1H, s), 7.86 (1H, d, J=8.0 Hz), 7.61 (1H, s), 7.32 (1H, d, J=8.8 Hz), 7.20 (1H, d, J=8.4 Hz), 6.89 (1H, d, J=9.2 Hz), 5.68 (1H, d, J=3.6 Hz), 5.01 (2H, d, J=6.4 Hz), 4.29-4.23 (4H, m), 4.15-4.12 (1H, m); ³¹P NMR: (D₂O) δ -10.24 (d, J=22 Hz), -10.34 (d, 7=21 Hz), -22.04 (t, J=48 Hz); FTIR: (neat) 3042, 2338, 1623, 1438, 1218, 1067, 916 cm⁻¹; HR-MS: (ESI) m/z calculated for (C₂₀H₂₂BrN₆O₁₄P₃—H)⁺ 740.9517 (⁷⁹Br) and 742.9501 (⁸¹Br), found 740.9515 (⁷⁹Br) and 742.9499 (⁸¹Br).

Example 10

7-Hydroxy-8-nitroquinaldine (5a)

Figure 19:
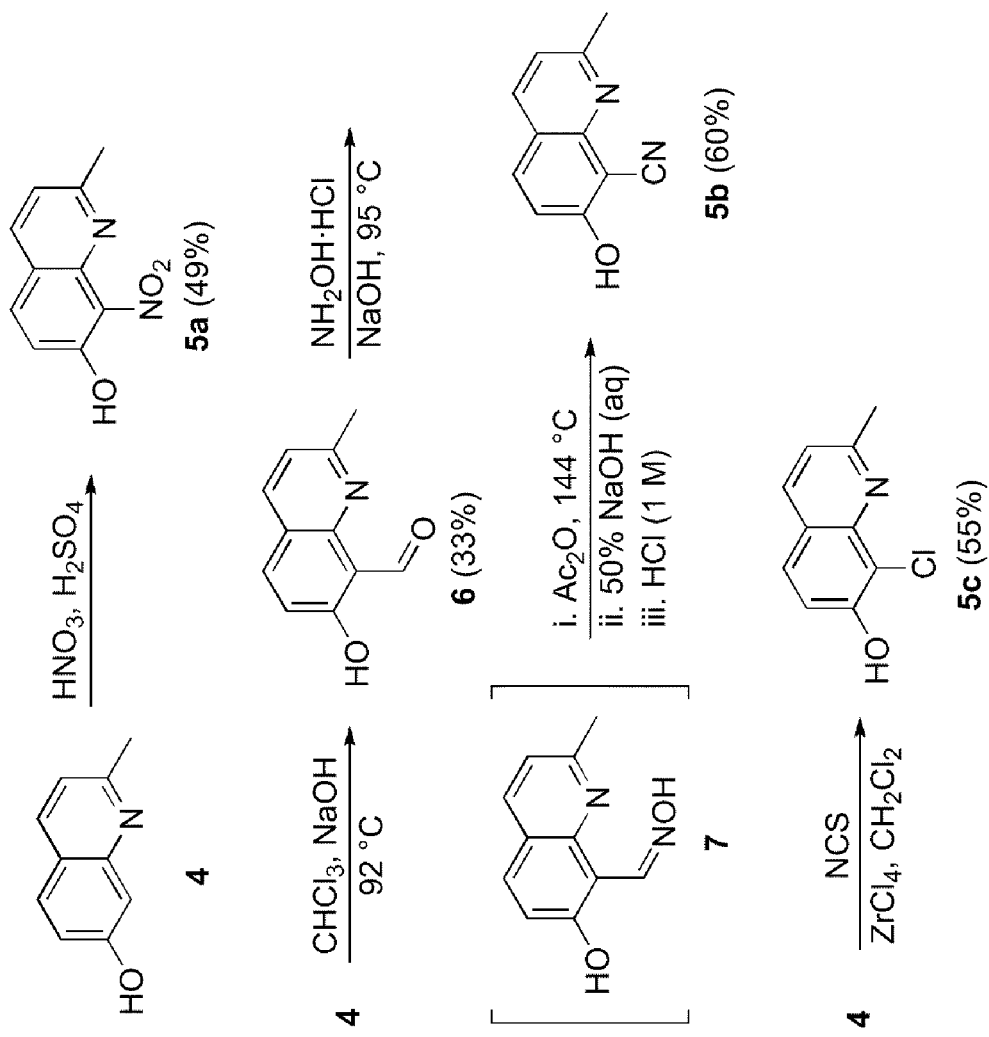
FIG. 19 schematically illustrates the synthesis of substituted quinolines 7-Hydroxy-8-nitroquinaldine (5a), 7-Hydroxy-2-methylquinoline-8-carbonitrile (5b), and 8-Chloro-7-hydroxyquinaldine (5c).

Referring to FIG. 19, concentrated HNO₃ (4 drops) was added to a solution of 7-hydroxyquinaldine (4, 200 mg, 1.258 mmol) concentrated H₂SO₄ (1.0 mL) at 0° C. and the mixture was stirred for 10 min. The reaction was neutralized with ammonium hydroxide and concentrated under vacuum. The remaining residue was dissolved in chloroform and the resulting clear solution was separated from the solid ammonium salts and concentrated to afford 5a (126 mg, 0.618 mmol, 49%) as a bright yellow solid: ¹H NMR (CD₃OD) δ 8.16 (1H, d, J=8.4 Hz), 7.84 (1H, d, J=8.8 Hz), 7.31 (1H, d, J=8.4 Hz), 7.20 (1H, d, J=8.8 Hz), 2.67 (3H, s); ¹³C NMR (DMSO-d₆) δ 161.8, 150.1, 140.7, 136.9, 134.7, 131.2, 121.6, 120.6, 118.5, 25.7; FTIR (neat) 2916, 2848, 1633, 1585, 1525, 1508, 1375, 1344, 841 cm⁻¹; MS (ESI) m/z calculated for (C₁₁H₈N₂O₃+H)⁺ 205, found 205; HRMS (ESI) m/z calculated for (C₁H₈N₂O₃+H)⁺ 205.0613, found 205.0600.

Example 11

7-(Methoxymethoxy)-8-nitroquinaldine (8a)

Figure 20:
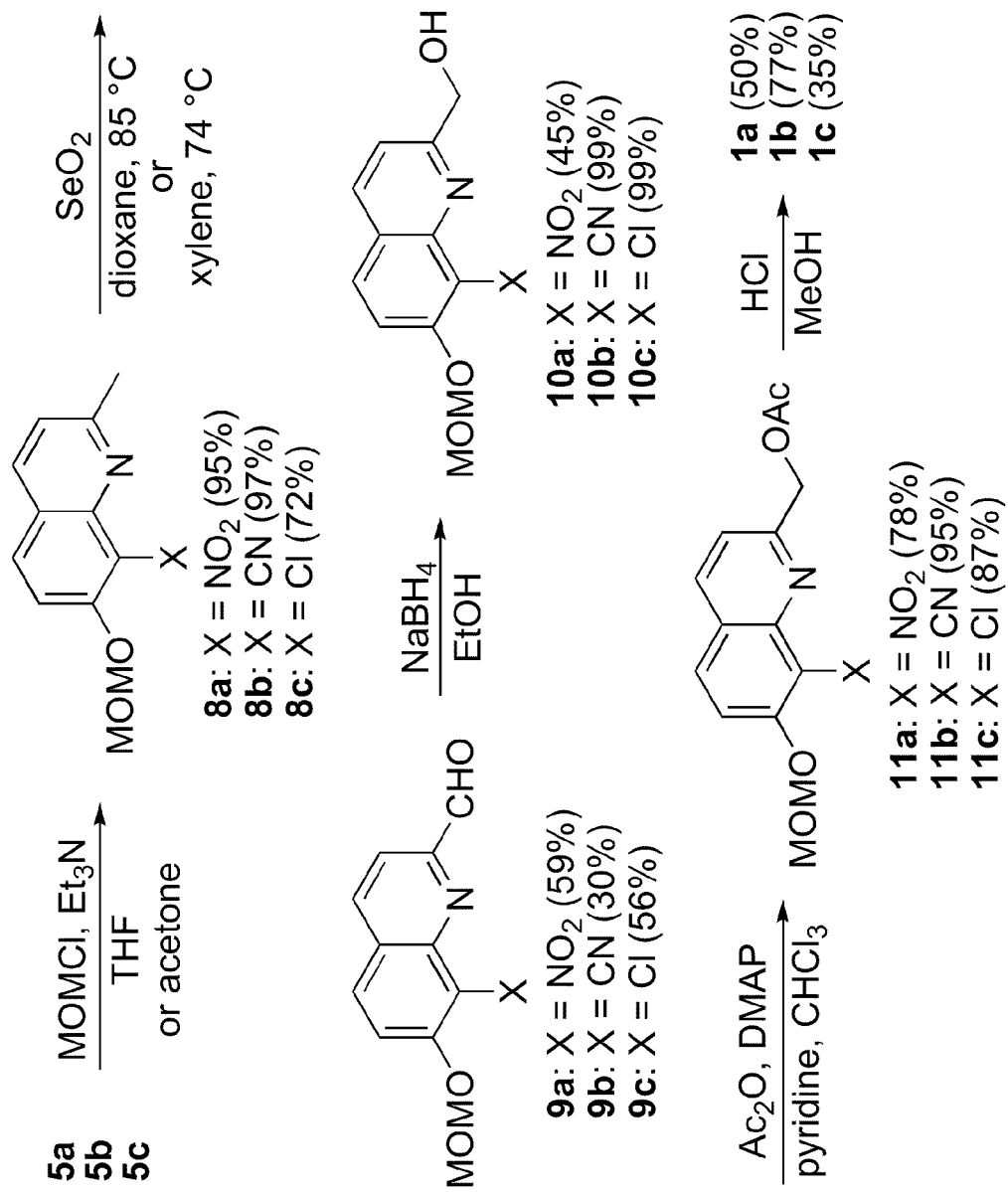
FIG. 20 schematically illustrates the synthesis of NHQ-OAc (11a), CyHQ-OAc (11b), and CHQ-OAc (11c).

Referring to FIG. 20, triethylamine (174 μL, 1.695 mmol) was added to a solution of 5a (174 mg, 0.847 mmol) in dry THF (5 mL) under a nitrogen atmosphere. Chloromethyl methyl ether (128 μL, 1.695 mmol) was added to the mixture dropwise and the reaction was stirred for 1 h. The reaction was diluted with chloroform, washed with water followed by brine. The organic layer was dried over Na₂SO₄, and the solvent was evaporated to afford 8a (200 mg, 0.806 mmol, 95%) as a bright yellow solid: ¹H NMR (CDCl₃) δ 8.00 (1H, d, J=8.4 Hz), 7.81 (1H, d, J=9.2 Hz), 7.47 (1H, d, J=8.8 Hz), 7.26 (1H, d, J=8.4 Hz), 5.35 (2H, s), 3.52 (3H, s), 2.69 (3H, s); ¹³C NMR (CDCl₃) δ 162.5, 148.3, 140.3, 137.7, 135.7, 130.3, 122.2, 122.2, 115.4, 95.3, 57.0, 25.9; FTIR (neat) 2955, 1626, 1525, 1508, 1377, 1247, 1226, 1193, 1153, 1065, 991, 924, 835, 806, 656 cm⁻¹; MS (ESI) m/z calculated for (C₁₂H₁₂N₂O₄+H)⁺ 249, found 249; HRMS (ESI) m/z calculated for (C₁₂H₁₂N₂O₄+H)⁺ 249.0875, found 249.0871.

Example 12

7-(Methoxymethoxy)-8-nitroquinolin-2-yl formaldehyde (9a)

Referring to FIG. 20, under a nitrogen atmosphere, selenium dioxide (11 mg, 0.099 mmol) was added to a solution of 8a (22.1 mg, 0.089 mmol) in dioxane (2 mL) at 85° C. The reaction was stirred for 20 h at 85° C., then cooled, diluted with methanol, and vacuum filtered. The filtrate was collected and concentrated, leaving a yellow solid, which was purified by column chromatography (4:6 EtOAc/hexane) to provide 9a (13.7 mg, 0.0523 mmol, 59%) as a yellow solid: ¹H NMR (CDCl₃) δ 10.15 (1H, s), 8.35 (1H, d, J=8.4 Hz), 8.02 (1H, d, J=8 Hz), 8.00 (1H, d, J=9.6 Hz), 7.76 (1H, d, J=9.2 Hz), 5.43 (2H, s), 3.56 (3H, s); ¹³C NMR (CDCl₃) δ 193.25, 154.14, 149.28, 140.47, 137.83, 137.55, 130.64, 125.26, 119.33, 117.34, 95.45, 57.24; FTIR (neat) 2858, 1715, 1529, 1263, 1197, 1155, 1061, 935, 918, 849, 806, 771, 658 cm⁻¹; MS (ESI) m/z calculated for (C₁₂H₁₀N₂O₅+H)⁺ 263, found 263; HRMS (ESI) m/z calculated for (C₁₂H₁₀N₂O₅+H)⁺ 263.0668, found 263.0662.

Example 13

7-(Methoxymethoxy)-8-nitroquinolin-2-yl methanol (10a)

Referring to FIG. 20, NaBH₄ was added to a solution of 9a (18.1 mg, 0.0691 mmol) in absolute EtOH (5 mL). The reaction mixture was stirred for 15 min, diluted with chloroform, washed with water followed by brine. The organic layer was dried over Na₂SO₄ and the solvent was evaporated to afford 10a (8.3 mg, 0.032 mmol, 45%) as a yellow solid: $^1$H NMR (CDCl$_3$) δ 8.14 (1H, d, J=8.8 Hz), 7.90 (1H, d, J=9.2 Hz), 7.58 (1H, d, J=9.2 Hz), 7.31 (1H, d, J=8.4 Hz), 5.39 (2H, s), 4.91 (2H, s), 3.54 (3H, s); $^{13}$C NMR (CDCl$_3$) δ 162.4, 149.0, 139.1, 136.7, 131.9, 130.6, 123.1, 118.5, 116.3, 95.4, 64.5, 57.1; FTIR (neat) 3583, 2923, 1635, 1516, 1263, 1157, 1084, 1047, 931, 916, 804 cm$^{-1}$; MS (ESI) m/z calculated for (C$_{12}$H$_{12}$N$_2$O$_5$+H)$^+$ 265, found 265; HRMS (ESI) m/z calculated for (C$_{12}$H$_{12}$N$_2$O$_5$+H)$^+$ 265.0824, found 265.0814.

Example 14

7-(Methoxymethoxy)-8-nitroquinolin-2-yl methyl acetate (1a)

Referring to FIG. 20, DMAP (10.2 mg, 0.083 mmol) and acetic anhydride (15 µL, 0.16 mmol) were added to a solution of 10a (8.3 mg, 0.032 mmol) in chloroform (4 mL) and pyridine (1 mL) under a nitrogen atmosphere. The reaction was stirred for 18 h. The solvent was evaporated and the residue was purified by column chromatography (3:7 EtOAc/hexane) to afford 11a (7.6 mg, 0.025 mmol, 78%) as a yellow solid: $^1$H NMR (CDCl$_3$) δ 8.16 (1H, d, J=8.4 Hz), 7.88 (1H, d, J=9.2 Hz), 7.56 (1H, d, J=9.2 Hz), 7.44 (1H, d, J=8.4 Hz), 5.37 (2H, s), 5.36 (2H, s), 3.53 (3H, s), 2.20 (3H, s); $^{13}$C NMR (CDCl$_3$) δ 170.8, 159.4, 148.7, 140.0, 137.7, 136.7, 130.4, 123.0, 119.0, 116.6, 95.3, 67.0, 57.1, 21.1; FTIR (neat) 2932, 1747, 1654, 1543, 1386, 1218, 1073, 810 cm$^{-1}$; MS (ESI) m/z calculated for (C$_{14}$H$_{14}$N$_2$O$_6$+H)$^+$ 307, found 307; HRMS (ESI) m/z calculated for (C$_{14}$H$_{14}$N$_2$O$_6$+H)$^+$ 307.0930, found 307.0930.

Example 15

7-Hydroxy-8-nitroquinolin-2-yl methyl acetate (NHQ-OAc, 1a)

Referring to FIG. 20, one drop of 12N HCl was added to a solution of 11a (7.0 mg, 0.023 mmol) in methanol (5 mL). The reaction was stirred for 10 min at room temperature followed by evaporation of the solvent. The resulting residue was taken up in chloroform, and the resulting clear solution was decanted and concentrated. The resulting residue was purified by column chromatography (1:1 EtOAc/hexane) to afford NHQ-OAc (3.0 mg, 0.0115 mmol, 50%) as a dark orange solid: $^1$H NMR (DMSO-d$_6$) δ 8.42 (1H, d, J=8.4 Hz), 8.04 (1H, d, J=9.2 Hz), 7.48 (1H, d, J=8.4 Hz), 7.41 (1H, d, J=8.8 Hz), 5.27 (2H, s), 2.15 (3H, s); $^{13}$C NMR (DMSO-d$_6$) 170.1, 158.5, 149.8, 139.5, 137.1, 133.9, 130.7, 120.7, 118.9, 117.7, 66.0, 20.5; FTIR (neat) 3076, 2922, 1740, 1637, 1527, 1506, 1450, 1375, 1342, 1304, 1213, 1140, 1063, 1028, 895, 844, 794, 656 cm$^{-1}$; MS (ESI) m/z calculated for (C$_{12}$H$_{10}$N$_2$O$_5$+H)$^+$ 263, found 263; HRMS (ESI) m/z calculated for (C$_{12}$H$_{10}$N$_2$O$_5$+H)$^+$ 263.0668, found 263.0651.

Example 16

7-Hydroxy-2-methylquinoline-8-carbaldehyde (6)

Referring to FIG. 19, chloroform (15 mL) was added to a mixture of 4 (1.0 g, 6.04 mmol) in a solution of NaOH (7 g in 8 mL water). The reaction was stirred at 92° C. for 20 h. After cooling, the reaction was filtered, washing with water, and the filtrate was extracted into chloroform, which was separated and evaporated to give a residue that was purified by column chromatography (1:1 EtOAc/hexane) to give 6 (0.380 g, 2.00 mmol, 33%) as a yellow solid: $^1$H NMR (acetone-d$_6$) δ 13.05 (1H, s), 11.20 (1H, s), 8.19 (1H, d, J=8.4 Hz), 8.14 (1H, d, J=9.2 Hz), 7.39 (1H, d, J=8.4 Hz), 8.10 (1H, d, J=9.2 Hz), 2.70 (3H, s); $^{13}$C NMR (acetone-d$_6$) δ 197.4, 165.9, 160.7, 148.3, 137.2, 136.3, 120.6, 120.0, 118.8, 112.6, 25.5; FTIR (neat) 2893, 1629, 1612, 1504, 1292, 1269, 1178, 1140, 781, 692, 662 cm$^{-1}$; MS (ESI) m/z calculated for (C$_{11}$H$_9$NO$_2$+H)$^+$ 188, found 188; HRMS (ESI) m/z calculated for (C$_{11}$H$_9$NO$_2$+H)$^+$ 188.0712, found 188.0746.

Example 17

7-Hydroxy-2-methylquinoline-8-carbaldehyde oxime (7)

Referring to FIG. 19, hydroxylamine hydrochloride (0.106 g, 1.52 mmol) was added to a mixture of 6 (0.200 g, 1.06 mmol) in a solution of NaOH (0.3 in 6 mL water). The reaction was stirred at 95° C. for 15 min followed by the addition of glacial acetic acid until it reached pH 6. The resulting mixture was cooled in an ice bath and vacuum filtered to afford 7 (0.176 g, 0.869 mmol, 82% yield) as a yellow solid, which was carried to the next step without further purification.

Example 18

7-Hydroxy-2-methylquinoline-8-carbonitrile (5b)

Referring to FIG. 19, compound 7 (0.160 g, 0.792 mmol) was added to acetic anhydride (3.5 mL) and the resulting mixture was stirred at 144° C. under nitrogen atmosphere for 7.5 h. Concentrated NaOH solution (50%) was added to the mixture slowly with stirring until the reaction reached pH 12. The solvent was evaporated and the resulting dark brown residue was purified by column chromatography (1:1 EtOAc/hexane) to yield 5b (0.0874 g, 0.475 mmol, 60%) as a yellow solid: $^1$H NMR (acetone-d$_6$) δ 8.20 (1H, J=8.0 Hz), 8.04 (1H, d, J=8.8 Hz), 7.37 (1H, d, J=8.4 Hz), 7.36 (1H, d, J=9.2 Hz), 2.69 (3H, s); $^{13}$C NMR (acetone-d$_6$) δ 163.1, 161.7, 149.1, 136.6, 133.9, 121.0, 117.3, 114.8, 95.7, 24.7; FTIR (neat) 3111, 2922, 2229, 1620, 1577, 1508, 1446, 1342, 1271, 1143, 844 cm$^{-1}$; MS (ESI) m/z calculated for (C$_{11}$H$_8$N$_2$O+H)$^+$ 185, found 185; HRMS (ESI) m/z calculated for (C$_{11}$H$_8$N$_2$O+H)$^+$ 185.0716, found 185.0766.

Example 19

7-(Methoxymethoxy)-2-methylquinoline-8-carbonitrile (8b)

Referring to FIG. 20, under a nitrogen atmosphere, triethylamine (0.034 mL, 0.235 mmol) and chloromethyl methyl ether (0.018 mL, 0.235 mmol) were added to a solution of 5b (0.0200 g, 0.109 mmol) in acetone (8 mL). The reaction was stirred for 1 h. The solvent was evaporated and the remaining residue was dissolved in chloroform, which was washed with brine, dried over Na$_2$SO$_4$, and evaporated to afford 8b (0.0236 g, 0.106 mmol, 97%) as a white solid: $^1$H NMR (CDCl$_3$) δ 8.02 (1H, d, J=8.0 Hz), 7.93 (1H, d, J=9.2 Hz), 7.48 (1H, d, J=9.2 Hz), 7.29 (1H, d, J=8.4 Hz), 5.43 (2H, s), 3.58 (3H, s), 2.79 (3H, s); $^{13}$C NMR (CDCl$_3$) δ 162.4, 161.8, 148.7, 135.9, 133.4, 121.8, 121.7, 114.6, 114.9, 95.1, 56.9, 25.7; FTIR (neat) 2924, 2216, 1612, 1504, 1248, 1161, 1143, 1061, 984, 924, 839 cm$^{-1}$; MS (ESI) m/z calculated for (C$_{13}$H$_{12}$N$_2$O$_2$+H)$^+$ 229, found 229; HRMS (ESI) m/z calculated for (C$_{13}$H$_{12}$N$_2$O$_2$+H)$^+$ 229.0978, found 229.0996.

Example 20

2-Formyl-7-(methoxymethoxy)quinoline-8-carbonitrile (9b)

Referring to FIG. 20, under a nitrogen atmosphere selenium dioxide (0.0145 g, 0.131 mmol) was added to a solution of 8b (0.0300 g, 0.136 mmol) in m-xylene (5 mL). The mixture was stirred at 74° C. for 20 h then filtered. The filtrate was evaporated, and the residue was purified by column chromatography (3:7 EtOAc/hexane) to yield 9b (0.0100 g, 0.041 mmol, 30%) as a white solid: $^1$H NMR (CDCl$_3$) δ 10.29 (1H, s), 8.34 (1H, d, J=8.0 Hz), 8.09 (1H, d, J=9.6 Hz), 8.04 (1H, d, J=8.0 Hz), 7.73 (1H, d, J=9.2 Hz), 5.50 (2H, s), 3.61 (3H, s); $^{13}$C NMR (CDCl$_3$) δ 193.7, 163.0, 154.2, 148.6, 137.9, 133.9, 125.4, 118.5, 117.3, 114.3, 95.4, 57.3; FTIR (neat) 2922, 2846, 2224, 1710, 1260, 1165, 1043, 922, 856, 775 cm$^{-1}$; MS (ESI) m/z calculated for (C$_{13}$H$_{10}$N$_2$O$_3$+H)$^+$ 243, found 243; HRMS (ESI) m/z calculated for (C$_{13}$H$_{10}$N$_2$O$_3$+H)$^+$ 243.0769, found 243.0764.

Example 21

2-(Hydroxymethyl)-7-(methoxymethoxy)quinoline-8-carbonitrile (10b)

Referring to FIG. 20, NaBH$_4$ (0.0151 g, 0.400 mmol) was added to a solution of 9b (0.0240 g, 0.099 mmol) in ethanol (5 mL). The mixture was stirred for 20 min. The solvent was evaporated and the resulting residue was dissolved in chloroform, then washed with water followed by brine, dried over Na$_2$SO$_4$, concentrated, and purified by column chromatography (45:55 EtOAc/hexane) to yield 10b (0.0240 g, 0.98 mmol, 99%) as a white solid: $^1$H NMR (CDCl$_3$) δ 8.14 (1H, d, J=8.0 Hz), 8.00 (1H, d, J=8.8 Hz), 7.56 (1H, d, J=9.6 Hz), 7.31 (1H, d, J=8.4 Hz), 5.46 (2H, s), 4.96 (2H, s), 3.59 (3H, s); $^{13}$C NMR (CDCl$_3$) δ 202.5, 162.4, 147.6, 137.1, 133.9, 122.9, 118.3, 115.6, 114.6, 95.3, 64.4, 57.2; FTIR (neat) 2926, 1738, 1258, 1078, 795 cm$^{-1}$; MS (ESI) m/z calculated for (C$_{13}$H$_{10}$N$_2$O$_3$+H)$^+$ 245, found 245; HRMS (ESI) m/z calculated for (C$_{13}$H$_{10}$N$_2$O$_3$+H)$^+$ 245.0922, found 245.0914.

Example 22

(8-Cyano-7-(methoxymethoxy)quinolin-2-yl)methyl acetate (11b)

Referring to FIG. 20, under a nitrogen atmosphere, DMAP (0.0102 g) and acetic anhydride (0.015 mL, 0.158 mmol) were added to a solution of 10b (0.0090 g, 0.0369 mmol) in chloroform (5 mL) and pyridine (1.5 mL). The reaction was stirred for 24 h. The solvents were evaporated, and the remaining residue was purified by column chromatography (3:7 EtOAc/hexane) to provide 11b (0.0100 g, 0.0351 mmol, 95% yield) as a white solid: $^1$H NMR (CDCl$_3$) δ 8.16 (1H, d, J=8.0 Hz), 7.98 (1H, d, J=9.2 Hz), 7.55 (1H, d, J=9.2 Hz), 7.44 (1H, d, J=8.4 Hz), 5.46 (2H, s), 5.45 (2H, s), 3.58 (3H, s), 2.26 (3H, s); $^{13}$C NMR (CDCl$_3$) δ 170.7, 162.2, 159.2, 148.2, 136.9, 133.5, 122.7, 118.5, 115.7, 114.5, 95.1, 66.7, 56.9, 21.0; FTIR (neat) 2924, 2342, 2224, 1738, 1612, 1508, 1246, 1157, 1070, 937, 846 cm$^{-1}$; MS (ESI) m/z calculated for (C$_{15}$H$_{14}$N$_2$O$_4$+H)$^+$ 287, found 287; HRMS (ESI) m/z calculated for (C$_{15}$H$_{14}$N$_2$O$_4$+H)$^+$ 287.1033, found 287.1059.

Example 23

(8-Cyano-7-hydroxyquinolin-2-yl)methyl acetate (CyHQ-OAc, 1b)

Referring to FIG. 20, 12N HCl (1 drop) was added to a solution of 11b (0.0100 g, 0.0350 mmol) in methanol (3 mL), and the mixture was stirred for 35 min. The solvent was evaporated, and the residue was purified by column chromatography (35:65 EtOAc/hexane) to yield CyHQ-OAc (0.0065 g, 0.0269 mmol, 77%) as a white solid: $^1$H NMR (CDCl$_3$) δ 8.14 (1H, d, J=8.4 Hz), 7.92 (1H, d, J=8.8 Hz), 7.42 (1H, d, J=8.8 Hz), 7.262 (1H, d, J=8.4 Hz), 5.45 (2H, s), 2.26 (3H, s); $^{13}$C NMR (CDCl$_3$) δ 171.37, 164.4, 158.9, 148.7, 137.4, 134.0, 121.8, 118.0, 117.5, 114.9, 66.4, 19.6; FTIR (neat) 2924, 2358, 2228, 1744, 1603, 1510, 1238, 1065, 849 cm$^{-1}$; MS (ESI) m/z calculated for (C$_{13}$H$_{10}$N$_2$O$_3$+H)$^+$ 243, found 243; HRMS (ESI) m/z calculated for (C$_{13}$H$_{10}$N$_2$O$_3$+H)$^+$ 243.0770, found 243.0788.

Example 24

8-Chloro-7-hydroxyquinaldine (5c)

Referring to FIG. 19, under a nitrogen atmosphere, 7-hydroxyquinaldine (4, 0.39 g, 2.452 mmol) was added to a solution of NCS (0.3283 g, 2.459 mmol) and zirconium chloride (0.0285 g, 0.122 mmol) in dichloromethane (35 mL). After stirring for 23 h, the solution was diluted with chloroform and washed successively with saturated sodium carbonate solution, water, and brine. The solvent was evaporated to give a brown residue, which was purified by column chromatography (1:3 EtOAc/hexane) to yield 5c (0.2612 g, 1.349 mmol, 55%) as an oily yellow residue: $^1$H NMR (CDCl$_3$) δ 8.00 (1H, d, J=8.0 Hz), 7.64 (1H, d, J=9.2 Hz), 7.28 (1H, d, J=8.0 Hz), 7.23, (1H, d, J=8.4 Hz), 2.80 (3H, s); $^{13}$C NMR (CDCl$_3$) δ 160.6, 152.8, 144.9, 136.6, 127.5, 122.7, 120.7, 117.0, 114.6, 25.9; FTIR (neat) 2926, 1619, 1509, 1437, 1343, 1267, 1215, 1141, 1002, 835, 750 cm$^{-1}$; MS (ESI) m/z calculated for (C$_{10}$H$_8$ClNO+H)$^+$ 194 ($^{35}$Cl) and 196 ($^{37}$Cl), found 194 ($^{35}$Cl) and 196 ($^{37}$Cl); HRMS (ESI) m/z calculated for (C$_{10}$H$_8$ClNO+H)$^+$ 194.0373 ($^{35}$Cl) and 196.0343 ($^{37}$Cl), found 194.0362 ($^{35}$Cl) and 196.0333 ($^{37}$Cl).

Example 25

8-Chloro-7-methoxymethylquinoline (8c)

Referring to FIG. 20, triethylamine (1.879 mL, 13.49 mmol) was added to a solution of 5c (0.2612 g, 1.349 mmol) in THF (20 mL) under a nitrogen atmosphere. Chloromethyl methyl ether (0.241 mL, 3.17 mmol) was added to the mixture dropwise. After stirring for 2 h, the solution was diluted with EtOAc and washed successively with water (×2) and brine. The organic layer was dried over MgSO$_4$, filtered, and evaporated. The resulting residue was purified by flash chromatography (3:7 EtOAc/hexane) to afford 8c (0.2298 g, 0.9668 mmol, 72%) as a yellow solid (mp 78-79° C.): $^1$H NMR (CDCl$_3$) δ 8.01 (1H, d, J=8.8 Hz), 7.67 (1H, d, J=8.8 Hz), 7.47 (1H, d, J=9.2 Hz), 7.26 (1H, d, J=8.8 Hz), 5.40 (2H, s), 3.58 (3H, s), 2.82 (3H, s); $^{13}$C NMR (CDCl$_3$) δ 160.9, 153.8, 145.4, 136.6, 126.9, 123.5, 121.4, 116.7, 105.0, 95.7, 56.8, 26.0; FTIR (neat) 2919, 1611, 1508, 1259, 1011, 833, 783 cm$^{-1}$; MS (ESI) m/z calculated for (C$_{12}$H$_{12}$ClNO$_2$+H)$^+$ 238

($^{35}$Cl) and 240 ($^{37}$Cl), found 238 ($^{35}$Cl) and 240 ($^{37}$Cl); HRMS (ESI) m/z calculated for $(C_{12}H_{12}ClNO_2+H)^+$ 238.0635 ($^{35}$Cl) and 240.0605 ($^{37}$Cl), found 238.0623 ($^{35}$Cl) and 240.0593 ($^{37}$Cl).

Example 26

8-Chloro-2-formyl-7-methoxymethylquinoline (9c)

Referring to FIG. 20, under a nitrogen atmosphere, selenium dioxide (0.0604 g, 0.544 mmol) was added to a solution of 8c (0.1232 g, 0.5184 mmol) in p-dioxane (3 mL), and the resulting orange solution was stirred in a sealed flask for 2 h at 85° C. The black precipitate was removed by vacuum filtration and the filtrand was evaporated, leaving a residue, which was purified by column chromatography (2:8 EtOAc/hexane) to afford 9c (0.0724 g, 0.288 mmol, 56%) as a pale yellow solid (mp 118-121° C.): $^1$H NMR (CDCl$_3$) δ 10.30 (1H, s), 8.30 (1H, d, J=8.0 Hz), 7.99, (1H, d, J=8.0 Hz), 7.81 (1H, d, J=9.6 Hz), 7.70 (1H, d, J=8.8 Hz), 5.45 (2H, s), 3.60 (3H, s); $^{13}$C NMR (CDCl$_3$) δ 193.9, 154.7, 153.4, 145.6, 138.0, 127.2, 127.0, 121.3, 120.2, 116.5, 95.7, 57.0; FTIR (neat) 2931, 2835, 1713, 1615, 1303, 1159, 1043, 920, 775 cm$^{-1}$; MS (ESI) m/z calculated for $(C_{12}H_{10}ClNO_3+H)^+$ 252 ($^{35}$Cl) and 254 ($^{37}$Cl), found 252 ($^{35}$Cl) and 254 ($^{37}$Cl); HRMS (ESI) m/z calculated for $(C_{12}H_{10}ClNO_3+H)^+$ 252.0427 ($^{35}$Cl) and 254.0398 ($^{37}$Cl), found 252.0418 ($^{35}$Cl) and 254.0390 ($^{37}$Cl).

Example 27

8-Chloro-2-hydroxymethyl-7-methoxymethylquinoline (10c)

Referring to FIG. 20, NaBH$_4$ (0.0028 g, 0.074 mmol) was added to a solution of 9c (0.0397 g, 0.158 mmol) in ethanol (4 mL). The mixture was stirred for 20 min. The solvent was evaporated, and the resulting solid residue was dissolved in chloroform, then washed with water (×2) followed by brine, dried over MgSO$_4$, and concentrated to afford 10c (0.0396 g, 0.156 mmol, 99%) as a white, crystalline solid (mp 84-87° C.): $^1$H NMR (CDCl$_3$) δ 8.09 (1H, d, J=8.4 Hz), 7.71 (1H, d, J=8.8 Hz), 7.52 (1H, d, J=9.2 Hz), 7.24 (1H, d, J=8.4 Hz), 5.41 (2H, s), 4.94 (2H, s) 3.58 (3H, s); $^{13}$C NMR (CDCl$_3$) δ 160.3, 154.2, 144.1, 137.2, 127.0, 124.4, 120.0, 117.4, 117.2, 95.7, 64.4, 56.8; FTIR (neat) 3342, 2925, 1615, 1155, 1005, 835, 781 cm$^{-1}$; MS (ESI) m/z calculated for $(C_{12}H_{12}ClNO_3+H)^+$ 254 ($^{35}$Cl) and 256 ($^{37}$Cl), found 254 ($^{35}$Cl) and 256 ($^{37}$Cl); HRMS (ESI) m/z calculated for $(C_{12}H_{12}ClNO_3+H)^+$ 254.0584 ($^{35}$Cl) and 256.0554 ($^{37}$Cl), found 254.0577 ($^{35}$Cl) and 256.0546 ($^{37}$Cl).

Example 28

(8-Chloro-7-(methoxymethoxy)quinolin-2-yl)methyl acetate (11c)

Referring to FIG. 20, under a nitrogen atmosphere, DMAP (0.0079 g), pyridine (1.0 mL), and acetic anhydride (0.121 mL, 1.28 mmol) were added to a solution of 10c (0.0630 g, 0.2483 mmol) in chloroform (4 mL). After stirring for 2 h, the solvents were evaporated and the remaining residue was purified by column chromatography (1:3 EtOAc/hexane) to afford 21c (0.0640 g, 0.216 mmol, 87%) as a white solid (mp 114-117° C.): $^1$H NMR (CDCl$_3$) δ 8.14 (1H, d, J=8.8 Hz), 7.71 (1H, d, J=9.2 Hz), 7.54 (1H, d, J=8.8 Hz), 7.42 (1H, d, J=8.0), 5.47 (2H, s), 5.41 (2H, s), 3.58 (3H, s), 2.23 (3H, s); $^{13}$C NMR (CDCl$_3$) δ 170.9, 157.8, 154.2, 145.2, 137.3, 127.0, 124.5, 120.4, 118.4, 117.8, 95.8, 67.6, 56.9, 21.2; FTIR (neat) 2937, 1745, 1619, 1514, 1379, 1245, 1058, 839, 783 cm$^{-1}$; MS (ESI) m/z calculated for $(C_{12}H_{12}ClNO_3+H)^+$ 254 ($^{35}$Cl) and 256 ($^{37}$Cl), found 254 ($^{35}$Cl) and 256 ($^{37}$Cl); HRMS (ESI) m/z calculated for $(C_{12}H_{12}ClNO_3+H)^+$ 254.0584 ($^{35}$Cl) and 256.0554 ($^{37}$Cl), found 254.0577 ($^{35}$Cl) and 256.0546 ($^{37}$Cl).

Example 29

(8-Chloro-7-hydroxyquinolin-2-yl)methyl acetate (CHQ-OAc, 1c)

Referring to FIG. 20, 12N HCl (1 drop) was added to a solution of 11c (0.0140 g, 0.0473 mmol) in methanol (3 mL), and the mixture stirred for 10 min. The solvent was evaporated, and the residue was purified by column chromatography (3:7 EtOAc/hexane) to afford CHQ-OAc (0.0042 g, 0.017 mmol, 35%) as a white solid (mp 126-127° C. dec): $^1$H NMR (CDCl$_3$) δ 8.13 (1H, d, J=8.5 Hz), 7.68 (1H, d, J=8.5 Hz) 7.40 (1H, d, J=8.5 Hz) 7.34 (1H, d, J=9.0 Hz) 5.46 (2H, s), 2.23 (3H, s); $^{13}$C NMR (CDCl$_3$) δ 171.0, 157.7, 153.2, 144.7, 137.4 127.6 123.8, 118.2, 117.8, 115.1, 67.5, 21.2; FTIR (neat) 2928, 1737, 1629, 1511, 1343, 1251, 850, 777 cm$^{-1}$; MS (ESI) m/z calculated for $(C_{12}H_{10}ClNO_3+H)^+$ 252 ($^{35}$Cl) and 254 ($^{37}$Cl), found 252 ($^{35}$Cl) and 254 ($^{37}$Cl); HRMS (ESI) m/z calculated for $(C_{12}H_{10}ClNO_3+H)^+$ 252.0427 ($^{35}$Cl) and 254.0398 ($^{37}$Cl), found 252.0420 ($^{35}$Cl) and 254.0390 ($^{37}$Cl).

Example 30

N,N,2-Trimethylquinolin-7-amine (13a)

Figure 21:
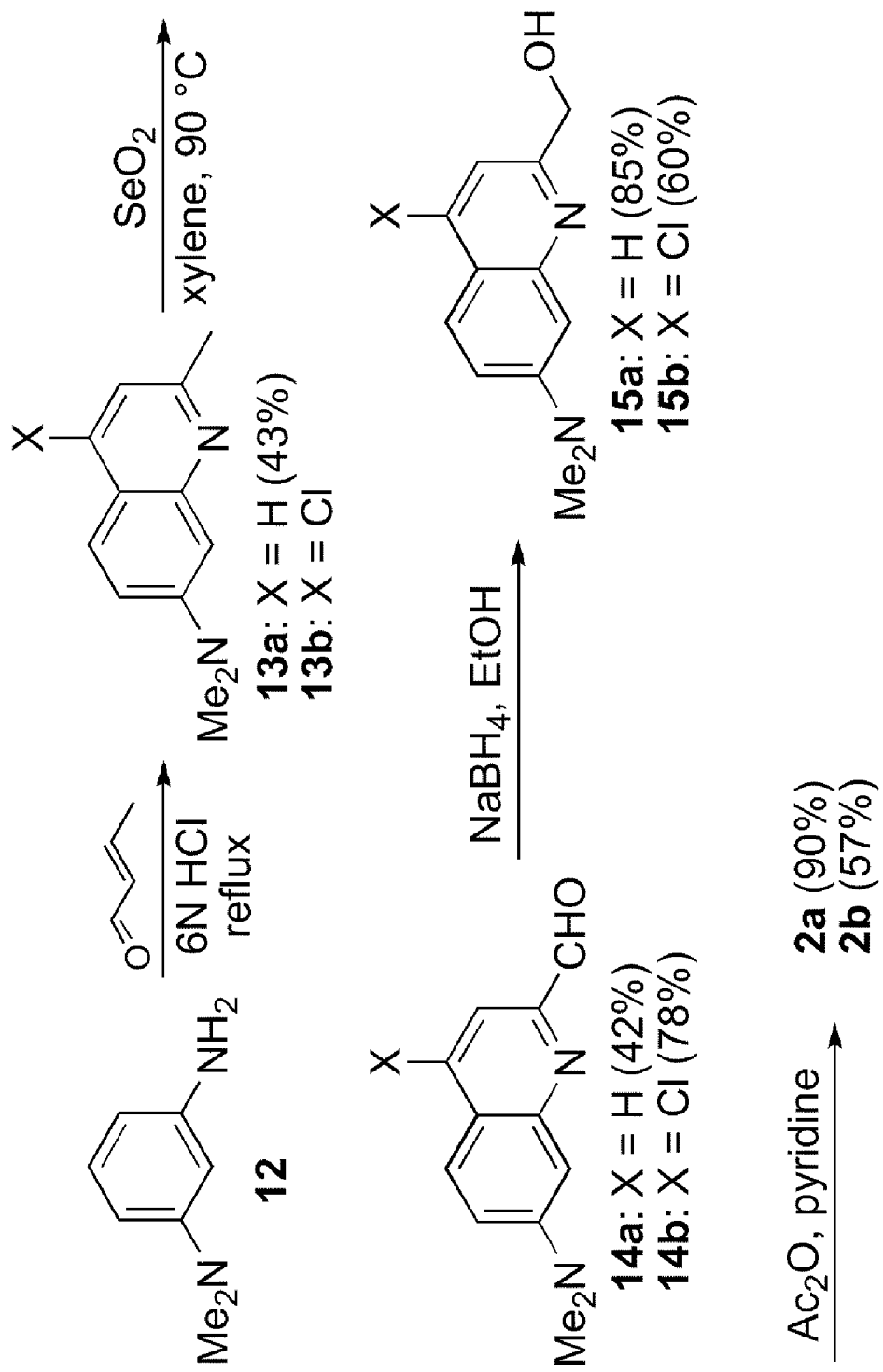
FIG. 21 schematically illustrates the synthesis of DMAQ-OAc (2a) and DMAQ-Cl-OAc (2b).

Referring to FIG. 21, a mixture of N,N-dimethyl-meta-phenylene-diamine (800 mg, 3.8 mmol) and 6 N HCl (12 mL) was stirred at reflux. Crotonaldehyde (0.31 mL, 3.8 mmol) dissolved in toluene (1 mL) was added dropwise to the purple solution. The reaction mixture was stirred for 2 h, cooled and neutralized with solid NaOH, and extracted with toluene, then chloroform (×5). The extracts were combined, dried over Na$_2$SO$_4$ and evaporated to dryness. The residue was purified by column chromatography (EtOAc) to obtain 13a (304.3 mg, 1.6 mmol, 43% yield): $^1$H NMR (CDCl$_3$) δ 7.84 (1H, d, J=8.4 Hz), 7.58 (1H, d, J=8.8 Hz), 7.09 (2H, m), 6.98 (1H, d, J=8. Hz), 3.06 (6H, s), 2.66 (3H, s); $^{13}$C NMR (CDCl$_3$) δ 159.3, 151.5, 149.9, 135.8, 128.6, 119.2, 118.2, 115.5, 106.8, 40.8, 25.6; FTIR (neat) 2918, 2804, 1620, 1600, 1514, 1379, 1155, 1062, 827 cm$^{-1}$.

Example 31

7-(Dimethylamino)quinoline-2-carbaldehyde (14a)

Referring to FIG. 21, compound 13a (304.3 mg, 1.63 mmol) was dissolved in m-xylenes (2 mL) and stirred under a nitrogen atmosphere. Selenium dioxide (272.29 mg 2.45 mmol) was added and the yellow-orange mixture was heated to 90° C. for 4 h. The black reaction mixture was filtered through cotton, washing several times with chloroform. The filtrate was directly adsorbed onto silica gel and purified by column chromatography (EtOAc) to afford 14a (136.4 mg, 0.68 mmol, 42%) as a pale yellow oil: $^1$H NMR (CDCl$_3$,) δ 10.11 (1H, s), 8.11 (1H, d, J=8.0 Hz), 7.74 (1H, d, J=8.4 Hz), 7.73 (1H, d, J=8.0 Hz), 7.31 (1H, dd, J=9.6, 2.8 Hz), 7.23 (1H, d, J=1.6 Hz), 3.15 (6H, s); $^{13}$C NMR (CDCl$_3$,) δ 194.5, 153.0, 151.9, 150.2, 136.9, 128.6, 123.1, 119.1, 113.8, 107.0, 40.7; FTIR (neat) 2920, 1705, 1620, 1537, 1508, 1382, 1255, 1155, 1066, 835, 761 cm$^{-1}$; MS (ESI) m/z calculated for $(C_{12}H_{12}N_2O+H)^+$ 201, found, 201; HRMS (ESI) m/z calculated for $(C_{12}H_{12}N_2O+H)^+$ 201.1028, found, 201.1055.

Example 32

7-(Dimethylamino)quinolin-2-yl)methanol (15a)

Referring to FIG. 21, compound 14a (45 mg, 0.22 mmol) was dissolved in absolute ethanol (0.7 mL) and the solution cooled with stirring in an ice bath. $NaBH_4$ (8.5 mg, 0.2248 mmol) was added in one portion to the cooled, stirred solution under nitrogen. The reaction was stirred at room temperature and monitored with TLC. The ethanol was evaporated and the residue dissolved in chloroform, washed with brine, and dried over $Na_2SO_4$. The solvent was evaporated and the remaining residue purified by column chromatography (EtOAc) to yield 14a (38.6 mg, 0.19 mmol, 85%) as a yellow oil: $^1H$ NMR $(CDCl_3)$ δ 7.95 (1H, d, J=8.4 Hz), 7.65 (1H, d, J=8.4 Hz), 7.15 (2H, m), 6.98 (1H, d, J=8.0 Hz), 4.84 (2H, s), 3.1 (6H, s); $^{13}C$ NMR $(CDCl_3)$ δ 159.0, 151.5, 148.6, 136.2, 128.3, 120.1, 115.7, 114.1, 106.5, 64.1, 40.5; FTIR (neat) 2918, 1622, 1535, 1508, 1394, 1284, 1207, 1174, 1134, cm$^{-1}$; MS (ESI) m/z calculated for $(C_{12}H_{14}N_2O+H)^+$ 203, found 203; HRMS (ESI) m/z calculated for $(C_{12}H_{14}N_2O+H)^+$ 203.1179, found 203.1177.

Example 33

(7-(Dimethylamino)quinolin-2-yl)methyl acetate (DMAQ-OAc, 2a)

Referring to FIG. 21, Compound 15a (38.6 mg, 0.191 mmol) was dissolved in pyridine (0.4 mL). Acetic anhydride (60 μL) was added and the mixture was stirred under nitrogen overnight. The pyridine was evaporated and the resulting residue was purified by column chromatography (9:1 EtOAc/hexane) to obtain DMAQ-OAc (42 mg, 0.17 mmol, 90% yield) as a bright yellow oil: $^1H$ NMR $(CDCl_3)$ δ 7.99 (1H, d, J=8.0 Hz), 7.65 (1H, d, J=9.2 Hz), 7.18 (1H, d, J=2.4 Hz), 7.16 (1H, d, J=3.2 Hz), 7.13 (1H, d, J=2.8 Hz), 5.31 (2H, s), 3.1 (6H, s), 2.18 (3H, s); $^{13}C$ NMR $(CDCl_3)$ δ 171.0, 156.4, 151.7, 149.8, 136.6, 128.4, 120.4, 116.6, 115.7, 106.8, 68.0, 40.7, 21.3; FTIR (neat) 2929, 1741, 1622, 1514, 1444, 1382, 1222, 1157, 1053, 829, 615 cm$^{-1}$; MS (ESI) m/z calculated for $(C_{14}H_{16}N_2O_2+H)^+$ 245, found 245; HRMS (ESI) m/z calculated for $(C_{14}H_{16}N_2O_2+H)^+$ 245.1285, found 245.1287.

Example 34

4-Chloro-7-(dimethylamino)quinoline-2-carbaldehyde (14b)

Referring to FIG. 21, 4-Chloro-N,N,2-trimethyl-quinolin-7-amine$^1$ (13b, 100 mg, 0.453 mmol) was dissolved in m-xylene (5 mL). Selenium dioxide (75 mg, 0.68 mmol) was added and the mixture was heated to 90° C. under nitrogen overnight. The hot reaction mixture was filtered through cotton and the filtrate was evaporated. The residue was dissolved in chloroform, adsorbed onto silica gel, and purified by column chromatography (chloroform) to provide 14b (83.1 mg, 0.35 mmol, 78%) as a yellow-orange solid: $^1H$ NMR $(CDCl_3)$ δ 10.11 (1H, s), 8.12 (1H, d, J=9.6 Hz), 7.77 (1H, s), 7.37 (1H, dd, J=8.8, 2.4 Hz), 7.23 (1H, d, J=2.8 Hz), 3.17 (6H, s); $^{13}C$ NMR $(CDCl_3)$ δ 193.5, 153.0, 152.4, 151.1, 143.9, 125.3, 120.5, 119.6, 114.0, 107.2, 40.7, 30.0; FTIR (neat) 2926, 2856, 1697, 1616, 1514, 1363, 1296, 1124, 846, 775 cm$^{-1}$; MS (ESI) m/z calculated for $(C_{12}H_{11}ClN_2O+H)^+$ 235, found 235; HRMS (ESI) m/z calculated for $(C_{12}H_{11}ClN_2O+H)^+$ 235.0638, found 235.0637.

Example 35

(4-Chloro-7-(dimethylamino)quinolin-2-yl)methanol (15b)

Referring to FIG. 21, compound 14b (50 mg, 0.213 mmol) was dissolved in absolute ethanol (2 mL). $NaBH_4$ (8 mg, 0.213 mmol) was added to the solution and the mixture was stirred for 30 min. The solvent was evaporated and the residue dissolved in methanol and filtered. The filtrate was adsorbed onto silica gel and purified by column chromatography (7:3 EtOAc/hexane) to obtain 15b (30 mg, 0.126 mmol, 60%). $^1H$ NMR $(CDCl_3)$ δ 8.02 (1H, d, J=8.8 Hz), 7.21 (1H, dd, J=9.2, 2.8 Hz), 7.11 (1H, d, J=2.8 Hz), 7.07 (1H, s), 4.81 (2H, s), 3.14, (6H, s); $^{13}C$ NMR $(CDCl_3)$ δ 159.4, 152.1, 149.6, 143.1, 125.1, 117.9, 116.5, 114.3, 106.3, 64.2, 40.6; FTIR (neat) 2918, 1622, 1535, 1508, 1394, 1284, 1207, 1174, 1134; MS (ESI) m/z calculated for $(C_{12}H_{13}ClN_2O+H)^+$ 237, found 237; HRMS (ESI) m/z calculated for $(C_{12}H_{13}ClN_2O+H)^+$ 237.0838, found 237.0832.

Example 36

(4-Chloro-7-(dimethylamino)quinolin-2-yl)methyl acetate (DMAQ-Cl-OAc, 2b)

Referring to FIG. 21, pyridine (0.6 mL) was added to 15b (30 mg, 0.126 mmol) and the solution was stirred under nitrogen for a few minutes before acetic anhydride (70 μL) was added dropwise. The solution was stirred under nitrogen for 17 h before the solvent was evaporated. The resulting residue was purified by column chromatography (3:7 EtOAc/hexane) to give DMAQ-Cl-OAc (20.0 mg, 71 μmol, 57%): $^1H$ NMR $(CDCl_3)$ δ 8.03 (1H, d, J=9.2 Hz), 7.23 (1H, d, J=9.2 Hz), 7.11 (1H, s), 7.14 (1H, s), 5.30 (2H, s), 3.14 (6H, s), 2.23 (3H, s); $^{13}C$ NMR $(CDCl_3)$ δ 170.6, 156.3, 151.9, 150.4, 143.0, 124.7, 117.9, 116.9, 115.4, 106.4, 67.1, 40.4, 21.0; FTIR (neat) 2992, 1744, 1616, 1514, 1425, 1373, 1225, 1132, 1053, 862, 845, 810, 756, 677 cm$^{-1}$; MS (ESI) m/z calculated for $(C_{12}H_{15}ClN_2O+H)^+$ 279, found 279; HRMS (ESI) m/z calculated for $(C_{12}H_{15}ClN_2O+H)^+$ 279.0900, found, 279.0934.

Example 37

O-2-Methylquinolin-7-yl dimethylcarbamothioate (16)

Figure 22:
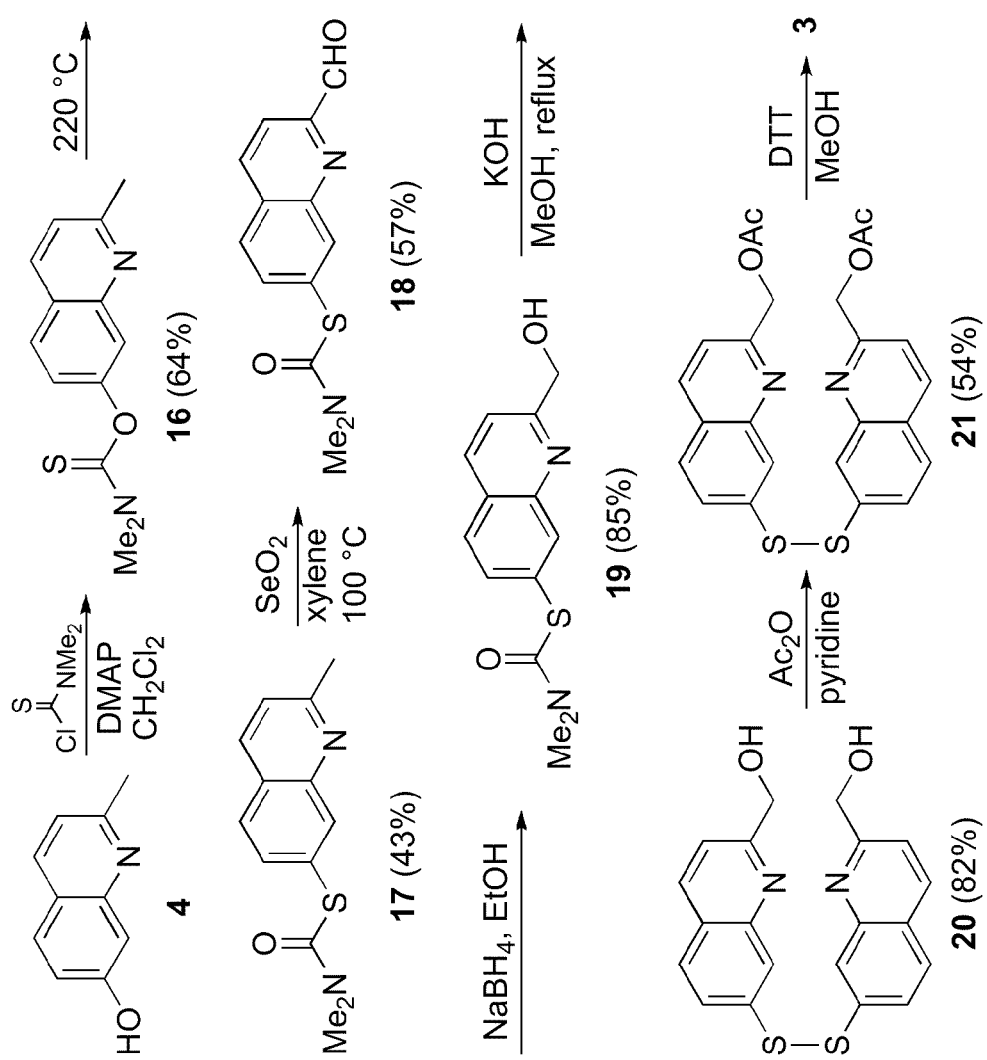
FIG. 22 schematically illustrates the synthesis of TQ-OAc (3), and precursors thereof.

Referring now to FIG. 22, under nitrogen, dimethylthiocarbamoyl chloride (1.35 g, 10.95 mmol) and DMAP (1.33 g, 10.95 mmol) were added to a suspension of 4 (300.0 mg, 0.628 mmol) in $CH_2Cl_2$ (6 mL). The dark brown solution was stirred for 24 h before it was diluted with chloroform and purified by column chromatography (4:6 to 1:1 EtOAc/hexane) to provide 16 (299 mg, 0.929 mmol, 64%) as an off-white solid: $^1H$ NMR $(CDCl_3)$ δ 8.05, (1H, d, J=8.4 Hz), 7.78 (1H, d, J=8.8 Hz), 7.67 (1H, d, J=2.4 Hz), 7.29 (1H, dd, J=8.0, 2.8 Hz), 7.27, (1H, dd, J=8.4, 3.6 Hz), 3.48 (3H, s), 3.40 (3H, s), 2.73 (3H, s); $^{13}C$ NMR $(CDCl_3)$ δ 187.6, 159.9, 154.7, 148.6, 136.2, 128.3, 124.8, 122.7, 122.1, 120.9, 43.5, 39.1, 25.6; FTIR (neat) 3379, 2940, 1624, 1603, 1531, 1504, 1393, 1283, 1206, 1169, 1130, 843, 748 cm$^{-1}$; MS (ESI) m/z calculated for $(C_{13}H_{14}N_2OS+H)^+$ 247, found 247; HRMS (ESI) m/z calculated for $(C_{13}H_{14}N_2OS+H)^+$ 247.0905, found 201.0900.

Example 38

S-2-Methylquinolin-7-yl dimethylcarbamothioate (17)

Referring now to FIG. 22, compound 16 (598 mg, 2.3 mmol) was heated to 220° C. for 2 h. The reaction was cooled and the dark solid residue obtained was dissolved in chloroform, adsorbed onto silica gel, and purified by column chromatography (1:1 to 4:6 EtOAc/hexane) to provide 17 (260 mg, 1.05 mmol, 43%) as an off-white solid: $^1$H NMR (CDCl$_3$) δ 8.17 (1H, d, J=8.8 Hz), 8.04, (1H, d, J=8.8 Hz), 7.78 (1H, d, J=8.4 Hz), 7.60 (1H, dd, J=8.4, 2.0 Hz), 7.31 (1H, d, J=8.8 Hz), 3.13 (3H, s), 3.04 (3H, s), 2.73 (3H, s); $^{13}$C NMR (CDCl$_3$) δ 166.6, 159.7, 147.9, 136.1, 135.6, 132.5, 130.6, 127.9, 126.7, 123.0, 37.2, 25.6; FTIR (neat) 2922, 1663, 1726, 1360, 1094, 843, 752, 689 cm$^{-1}$; MS (ESI) m/z calculated for (C$_{13}$H$_{14}$N$_2$OS+H)$^+$ 247, found 247; HRMS (ESI) m/z calculated for (C$_{13}$H$_{14}$N$_2$OS+H)$^+$ 247.0905, found 247.0904.

Example 39

S-2-Formylquinolin-7-yl dimethylcarbamothioate (18)

Referring now to FIG. 22, under a nitrogen atmosphere, selenium dioxide (67.3 mg, 0.606 mmol) was added to a solution of 17 (99.1 mg, 0.4027 mmol) in xylenes (3 mL). The mixture was heated to 100° C. for 3 h, then filtered hot through cotton, rinsing with chloroform. The product was adsorbed onto silica gel and purified by column chromatography (4:6 EtOAc/hexane) to afford 18 (60 mg, 0.230 mmol, 57%) as a white solid: $^1$H NMR (CDCl$_3$) δ 10.21 (1H, s), 8.41 (1H, d, J=8.8 Hz), 8.33 (1H, d, J=8.4 Hz), 8.06 (1H, d, J=8.8 Hz), 7.91 (1H, d, J=8.8 Hz), 7.80 (1H, dd, J=1.6, 8.4 Hz) 3.17 (3H, s), 3.07 (3H, s); $^{13}$C NMR (CDCl$_3$) δ 193.6, 165.8, 152.9, 147.7, 137.2, 136.8, 135.6, 132.21, 129.9, 127.9, 118.1, 37.0; FTIR (neat) 2922, 2876, 1705, 1661, 1366, 853, 758 cm$^{-1}$; MS (ESI) m/z calculated for (C$_{13}$H$_{12}$N$_2$O$_2$S+H)$^+$ 261, found 261; HRMS (ESI) m/z calculated for (C$_{13}$H$_{12}$N$_2$O$_2$S+H)$^+$ 261.0692, found 261.0661.

Example 40

S-2-(Hydroxymethyl)quinolin-7-yl dimethylcarbamothioate (19)

Referring now to FIG. 22, NaBH$_4$ (6.2 mg, 0.165 mmol) was added to a solution of 18 (43.1 mg, 0.165 mmol) in ethanol (1 mL), and the resulting mixture was stirred at room temperature. After TLC indicated the reaction was complete, the solvent was evaporated and the residue obtained was dissolved in chloroform. The solution was then washed with brine (×2), dried over Na$_2$SO$_4$, and evaporated to provide 19 (36.5 mg, 0.139 mmol, 85% yield) was obtained and carried to the next step without further purification.

Example 41

(7,7'-Disulfanediylbis(quinoline-7,2-diyl))dimethanol (20)

Referring now to FIG. 22, a solution of KOH (50 mg, 0.19 mmol) in methanol (1 mL) was added to a solution of 19 (50 mg, 0.19 mmol) in methanol (2 mL) and the resulting mixture was refluxed under a nitrogen atmosphere until the reaction was complete as indicated by TLC. The solvent was evaporated and the yellow residue obtained was neutralized with 1N HCl and extracted with chloroform. The organic layer was dried over Na$_2$SO$_4$. The solvent was evaporated to give a red solid, which was purified by column chromatography (25:1 chloroform/methanol) to obtain 20 (29.5 mg, 77 μmol, 82%) as a yellow solid: $^1$H NMR (CDCl$_3$) δ 8.22 (1H, s), 8.097 (1H, d, J=8.8 Hz), 7.79 (1H, d, J=8.4 Hz), 7.69 (1H, dd, J=8.4, 1.6 Hz), 7.25 (1H, d, J=8.4 Hz), 4.88 (2H, s); $^{13}$C NMR (CDCl$_3$) δ 156.0, 146.9, 138.7, 136.6, 128.6, 126.6, 125.8, 125.1, 118.4, 64.1; FTIR (neat) 2922, 2852, 1664, 1610, 1494, 1361, 1257, 1130, 1097, 906, 844, 688 cm$^{-1}$; MS (ESI) m/z calculated for (C$_{20}$H$_{16}$N$_2$O$_2$S$_2$+H)$^+$ 381, found 381; HRMS (ESI) m/z calculated for (C$_{20}$H$_{16}$N$_2$O$_2$S$_2$+H)$^+$ 381.0726, found 381.0734.

Example 42

(7,7'-Disulfanediylbis(quinoline-7,2-diyl))bis(methylene) diacetate (21)

Referring now to FIG. 22, acetic anhydride (250 μL) was added to a solution of 20 (15.5 mg, 0.0407 mmol) in pyridine (1 mL). The solution was stirred under nitrogen for 18 h at room temperature. Evaporation of the pyridine under vacuum left a residue that was dissolved in chloroform, adsorbed onto silica gel, and purified by column chromatography (3:7 to 4:6 EtOAc/hexane) to obtain 21 (10.2 mg, 22 μmol, 54%) as a white solid: $^1$H NMR (CDCl$_3$) δ 8.22 (1H, s), 8.13 (1H, d, J=8.4 Hz), 7.77 (1H, d, J=8.8 Hz), 7.67 (1H, dd, J=8.8, 1.6 Hz), 7.43 (1H, d, J=8.4 Hz), 5.33 (2H, s), 2.17 (3H, s); $^{13}$C NMR (CDCl$_3$) δ 170.9, 157.3, 148.0, 138.9, 137.0, 128.7, 126.7, 126.2, 125.6, 119.8, 67.5, 21.2; FTIR (neat) 2924, 2852, 1743, 1608, 1496, 1375, 1234, 1222, 1053, 844, 758 cm$^{-1}$; MS (ESI) m/z calculated for (C$_{24}$H$_{20}$N$_2$O$_4$S$_2$+H)$^+$ 465, found 465; HRMS (ESI) m/z calculated for (C$_{24}$H$_{20}$N$_2$O$_4$S$_2$+H)$^+$ 465.0942, found 465.0914.

Example 43

(7-Mercaptoquinolin-2-yl)methanol (TQ-OAc, (3))

Referring now to FIG. 22, DTT (27.3 mg) was added in three portions to a suspension of 21 (3.5 mg, 7.5 μmol) in methanol (1 mL). After 1 h, the solid dissolved producing an orange solution. Stirring was continued for 3 h until the reaction, which was monitored by HPLC (65% water (0.1% TFA) and 35% acetonitrile), was complete. MS analysis of the peaks as they eluted from the column revealed that monomer 3 had a retention time of 5.9 min, while 21 eluted at 15 min. The methanol was evaporated and the resulting solid mixture of DTT and 3 was dissolved in chloroform and washed with brine (×10) to remove DTT. The organic layer was dried over Na$_2$SO$_4$ and the chloroform evaporated to give approximately 1 mg of TQ-OAc. This product was unstable in air and easily oxidized to the disulfide. Alternatively, the solid mixture of DTT and 3 was dissolved in methanol and directly used in the photochemical experiments.

Example 44

Determination of the Quantum Efficiency for One-Photon Photolysis

KMOPS-buffered solutions (3 mL) of the substrates (100 μM) in quartz cuvettes (21-Q-10, Starna, Atascadero, Calif.) were irradiated with 365 nm UV light from a mercury lamp (Spectroline SB-100P; Spectronics, Westbury, N.Y.) with a light filter. The spectral output of the lamp after the glass filters (CSO-52 and CS7-60, Ace Glass, Vineland, N.J.) has a band between 350 nm and 380 nm. The duration of each irradiation period ranged from 5 sec to 60 sec. After each period of irradiation, a 20 μL aliquot of the solution was removed for analysis by HPLC, using an external standard method to determine concentrations.

TABLE 1

HPLC solvent conditions for analysis of quinoline-caged compounds

| Compound | $t_R$ (min) | $\lambda_{obs}$ (nm)* | Mobile Phase |
|---|---|---|---|
| BHQ-ATP (159) | 4.4 | 320 | 85:15 25 mM $KH_2PO_4$ water solution/methanol |
| ATP | 2.8 | 253 | 85:15 25 mM $KH_2PO_4$ water solution/methanol |
| NHQ-OAc (1a) | 7.9 | 320 | 65:35 acetonitrile/water (0.1% TFA) |
| CyHQ-OAc (1b) | 6.4 | 320 | 35:65 acetonitrile/water (0.1% TFA) |
| CHQ-OAc (1c) | 5.9 | 310 | 40:60 acetonitrile/water (0.1% TFA) |
| DMAQ-OAc (2a) | 6.8 | 438 | 40:60 acetonitrile/water (0.1% TFA) |
| DMAQ-Cl—OAc (2b) | 6.2 | 445 | 50:50 acetonitrile/water (0.1% TFA) |
| TQ-OAc (3) | 5.8 | 330 | 35:65 acetonitrile/water (0.1% TFA) |

*Detector observation wavelength

The analytes were eluted isocratically (flow rate of 1 mL/min) with acetonitrile and water containing 0.1% TFA (Table 1). The only exception is that BHQ-caged ATP was eluted with methanol and 25 mM $KH_2PO_4$ buffer (pH=6.2). The progress curves were plotted and fit to a single exponenial decay curve. The uncaging quantum efficiency ($Q_u$) of each chromophore was calculated using $Q_u = (I\sigma t_{90\%})^{-1}$, where I is the radiant power in einstein·cm$^{-2}$s$^{-1}$, $\sigma$ is the decadic extinction coefficient ($10^3 \times \epsilon$, molar extinction coefficient) in cm$^{-2}$·mol$^{-1}$, and $t_{90\%}$ is the irradiation time in s for 90% conversion to product (as described by Adams et al. (*J. Am. Chem. Soc.* (1988) 110: 3212-3220) incorporated herein by reference in its entirety). The UV intensity of the lamp was measured by potassium ferrioxalate actinometry (as described by Hatchard & Parker (*Proc. Roy. Soc. London*, Ser. A (1956) 235: 518-536) incorporated herein by reference in its entirety) in the same setup. ATP was monitored for its formation during the process, plotted, and fitted to an exponential rise to max curve.

Example 45

Determination of the Dark Hydrolysis Rate

Substrates were dissolved in KMOPS and stored in the dark at room temperature. Samples for HPLC analysis were carried out periodically and injected as described for one-photon photolysis. Data were fit to single exponential decay curves from which the time constant, $\tau$, was calculated. In a separate experiment, an NMR sample of BHQ-ATP in $D_2O$ was stable over the course of two weeks.

Example 46

Measurement of the Two-Photon Uncaging Action Cross-Section

Measurements were carried out in microcuvettes (10×1×1 mm illuminated dimensions) with an effective filling volume of 20 µL (26.10F-Q-10, Starna, Atascadero, Calif.). The IR laser used was from a fs-pulsed and mode-locked Ti:sapphire laser (Mira 900 pumped by a Verdi, Coherent, Santa Clara, Calif. or a Chameleon Ultra II) focused on the center of the cuvette chamber with a 25-mm focal length lens optimized for IR lasers (06LXP003/076, Melles-Griot, Irvine, Calif.). The pulse width of the laser was 144 fs for Mira 900. The laser beam was attenuated by passing the beam through an electro-optical modulator or a ½-waveplate and polarizing beam-splitter cube so that the average power exiting the apparatus was 300-350 mW.

Successive aliquots (25 µL) of each caged compound in KMOPS were placed into the cuvette and irradiated for 0, 5, 10, 20, and 40 min. Each aliquot was analyzed by HPLC to determine the concentration of the remaining caged compound as described for determining the uncaging quantum efficiency for one photon photolysis. The progress curves were plotted, and fitted to a single exponential decay curve. The formation of ATP was monitored, plotted, and fitted to a single exponential rise to max curve. For compounds 1c, 2a, 2b, and 3 ($\tau_{dark}$<50 h), a correction was made for background dark hydrolysis that occurred while the irradiated samples were waiting for HPLC analysis. The fraction of the decay from hydrolysis in the dark was calculated using the measured dark hydrolysis rate and the waiting time from the end of the experiment until the HPLC injection. This value was subtracted from the total decay (hydrolysis+photolysis) measured by HPLC. For compounds with dark >50 h, dark hydrolysis did not measurably impact the concentration determination.

The two-photon uncaging cross-section ($\delta_u$) was determined using Tsien's method, (as described by Furuta et al., (1999) Proc. Natl. Acad. Sci. U.S.A. 96: 1193-1200 (incorporated herein by reference in its entirety), referencing to fluorescein, a compound with a known fluorescence quantum yield ($Q_f$=0.9) and absorbance cross-section ($\delta_a$=30 GM at 740 nm), using the following equation:

$$\delta_u = \frac{N_p \phi Q_f \delta_a C_F}{<F(t)> C_S}$$

Figure 23:
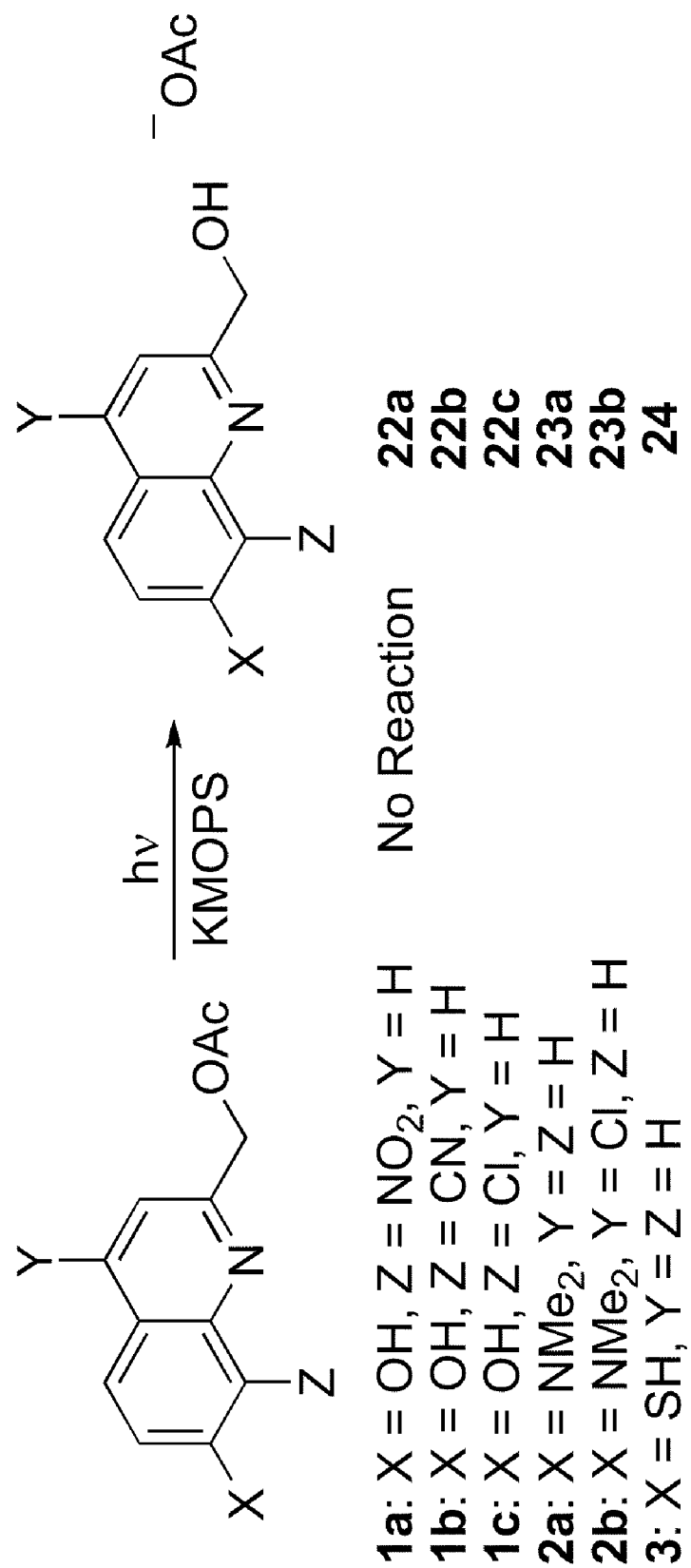
FIG. 23 illustrates the photolysis reaction of quinoline-protected acetates.

$N_p$ is the number of molecules photolyzed per unit time (molecules/s, determined by HPLC analysis of the reaction); $\phi$ is the collection efficiency of the detector (SED033 on an IL-1700, International Light, Newburyport, Mass.) used to measure the fluorescence of fluorescein emitted at a right angle to the beam and passed though a 535/45 nm bandpass filter; CF is the concentration of the fluorescein standard (mol/L); <F(t)> is the time averaged fluorescent photon flux (photons/s) of the fluorescein standard collected by the detector; and $C_S$ is the initial concentration of the caged compound (mol/L). The light-induced uncaging of —OAc from a variety of caging moieties is illustrated in FIG. 23.

Example 47

Chromophore Properties

TABLE 2

Photophysical and photochemical properties of quinoline chromophores[a]

| Chromophore | $\lambda_{max}$ (nm) | $\epsilon$ ($M^{-1} \cdot cm^{-1}$) | $\lambda_{em}$[b] (nm) | $Q_u$[c] | Sensitivity $Q_u \times \epsilon$ | $\delta_u$ (GM)[d] | $\lambda_a$[e] (GM)[e] | $\tau_{dark}$[f] (h) |
|---|---|---|---|---|---|---|---|---|
| BHQ-ATP | 376 | 1300 | — | 0.19 | 247 | 0.17 | 0.9 | >1000 |
| BHQ-OAc | 369[g] | 2600[g] | 478 | 0.29[g] | 754 | 0.59[g] | 2.0 | 71[g] |
| NHQ-OAc (1a) | 350 | 6500 | — | 0.00 | 0 | 0.00 | — | 278 |
| CyHQ-OAc (1b) | 364 | 7700 | 436 | 0.31 | 2387 | 0.32 | 1.0 | 500 |

TABLE 2-continued

Photophysical and photochemical properties of quinoline chromophores[a]

| Chromophore | $\lambda_{max}$ (nm) | $\epsilon$ (M$^{-1}$·cm$^{-1}$) | $\lambda_{em}$[b] (nm) | $Q_u$[c] | Sensitivity $Q_u \times e$ | $\delta_u$ (GM)[d] | $\lambda_a^e$ (GM)[e] | $\tau_{dark}$[f] (h) |
|---|---|---|---|---|---|---|---|---|
| CHQ-OAc (1c) | 370 | 2800 | 492 | 0.10 | 280 | 0.12 | 1.2 | 49 |
| DMAQ-OAc (2a) | 368 | 4600 | 496 | 0.046 | 211 | 0.13 | 2.8 | 31 |
| DMAQ-Cl—OAc (2b) | 386 | 3300 | 493 | 0.090 | 234 | 0.47 | 5.2 | 34 |
| TQ-OAc (3) | 369 | 5200 | — | 0.063 | 328 | 0.42 | 6.7 | 29 |

[a] Measured in KMOPS, pH 7.2.
[b] $l_{ex}$ = 365 nm.
[c] Measured at 365 nm.
[d] Measured at 740 nm, GM = $10^{-50}$ (cm$^4$·s)/photon.
[e] Calculated 2-photon absorbance cross-section, $d_u = d_a \times Q_u$.
[f] Time constant for hydrolysis in the dark.
[g] Value taken from Fedoryak, O. D.; Dore, T. M. Org. Lett. 2002, 4, 3419-3422.

Example 48

Figure 17:
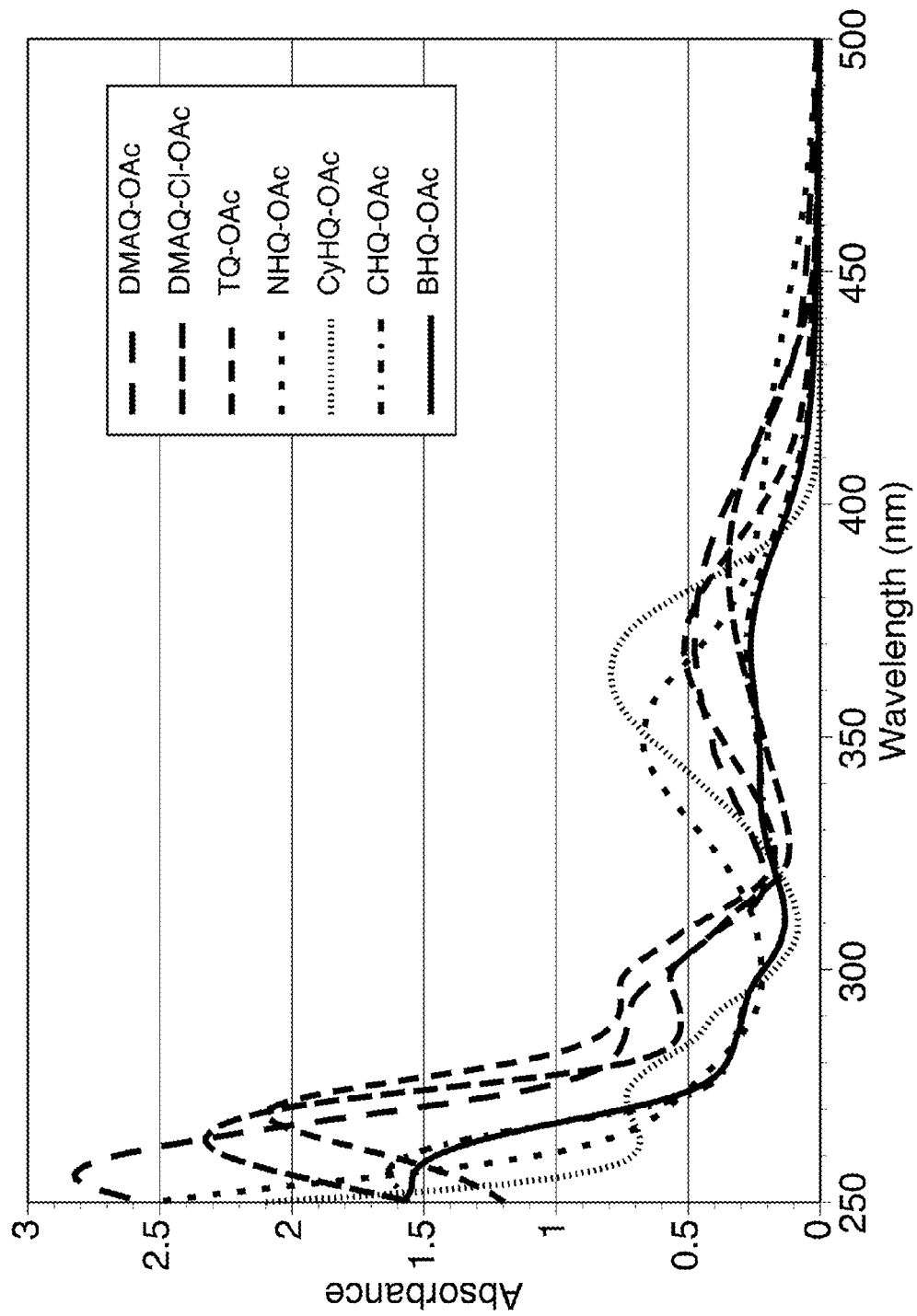
FIG. 17 is a graph comparing the UV and visible spectra of BHQ-OAc (120), NHQ-OAc (1a), CyHQ-OAc (1b), CHQ-OAc (1c), DMAQ-OAc (2a), DMAQ-Cl-OAc (2b), and TQ-OAc.
Figure 18:
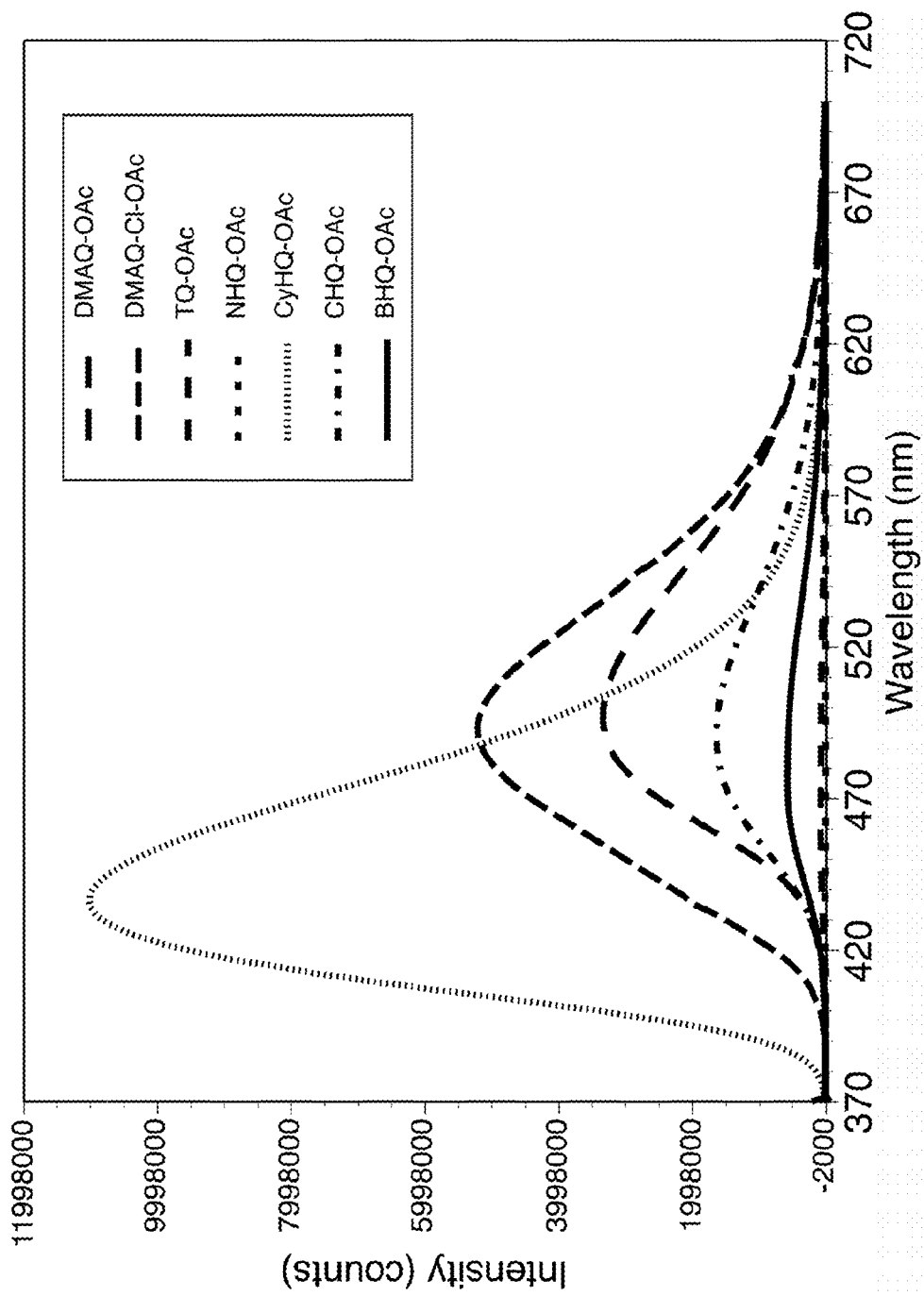
FIG. 18 is a graph showing the fluorescence spectra of BHQ-OAc (120), NHQ-OAc (1a), CyHQ-OAc (1b), CHQ-OAc (1c), DMAQ-OAc (2a), DMAQ-Cl-OAc (2b), and TQ-OAc (15 μM in KMOPS, $\lambda_{ex}$=365 nm).

Substituent Effects on the UV-Vis and Fluorescence Spectra of Quinoline Chromophores The UV-Vis spectra of BHQ-OAc, NHQ-OAc, CyHQ-OAc, CHQ-OAc, DMAQ-OAc, DMAQ-Cl-OAc, and TQ-OAc are shown in FIG. 17. The fluorescence spectra of BHQ-OAc, NHQ-OAc, CyHQ-OAc, CHQ-OAc, DMAQ-OAc, DMAQ-Cl-OAc, and TQ-OAc (15 μM in KMOPS, $\lambda_{ex}$=365 nm) are shown in FIG. 18.

Example 49

Figure 24A:
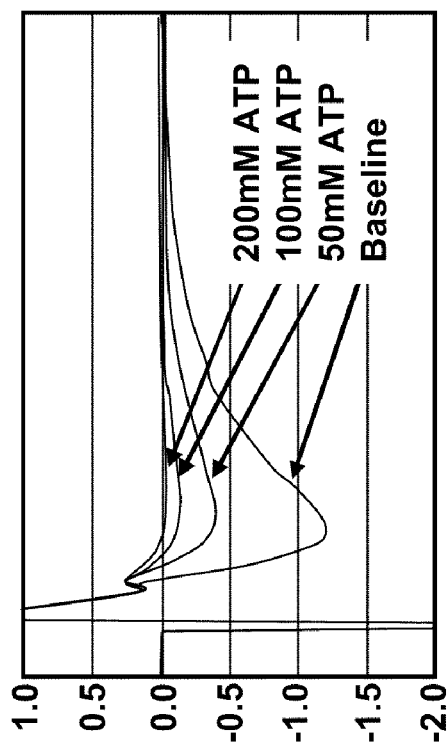
FIGS. 24A and 24B are graphs illustrating electrophysiology in a brain slice.
Figure 24B:
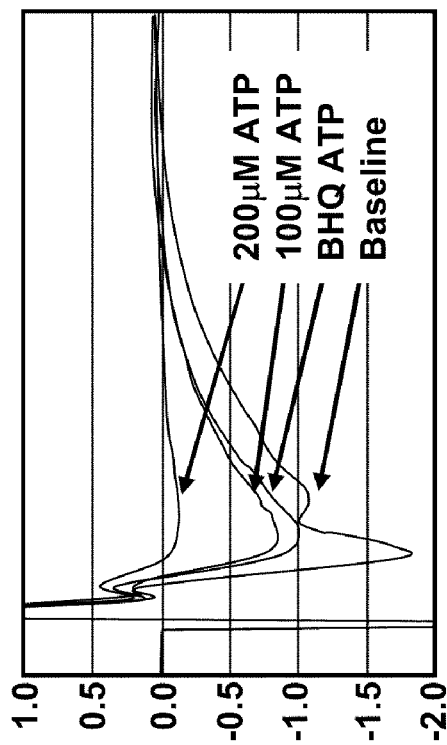

Electrophysiology in brain slice preparations were used as a means of testing the activity of BHQ-caged ATP, calcium, and neurotransmitters, as shown in FIGS. 24A and 24B. This approach enabled the direct application and measurement of the bioactivity of caged neuromodulators before, during, and after uncaging on the millisecond timescale. In this experiment, hippocampal slices were prepared from male Sprague-Dawley rats following established protocols. A bipolar stimulating electrode was placed on the CA3-side of the CA1 region in the stratum radiatum, and a recording microelectrode was then positioned in the same layer in CA1. Stimulus-response curves were obtained using stimulus pulses consisting of a single square wave of 270 ms duration delivered at 40-160 mA. The stimulation intensity was adjusted to obtain a field Excitatory Post Synaptic Potential (fEPSP) amplitude of 1.0-1.5 mV to begin baseline recording, and fEPSPs were elicited by stimulation of the Schaffer collateral-commissural pathway in stratum radiatum once every 60 s for the duration of the experiment. Synaptic responses were normalized by dividing all slopes by the average of the 5 fEPSP slopes obtained from the 5 min prior to drug delivery.

Prior to uncaging, BHQ-ATP produced little to no suppression in fEPSP; however, exposure of the preparation to 365-nm light produced a suppression in fEPSP similar to that seen with 50 μM of uncaged ATP (FIG. 24B), demonstrating that BHQ-ATP is biologically active upon uncaging.

Example 50

Imaging

Figure 26A:
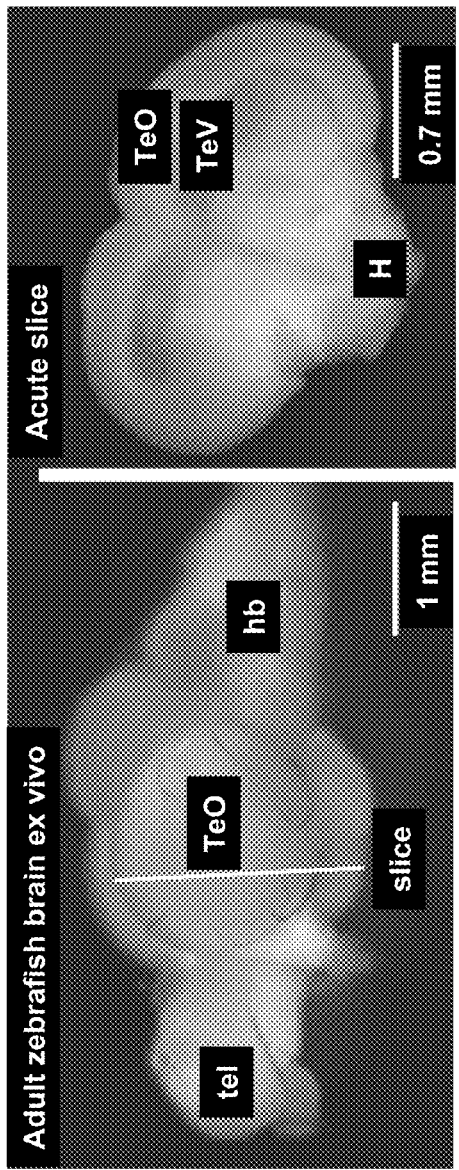
FIG. 26A is a pair of digital images showing chameleon expression in zebrafish adult whole brain (left) and brain slice (right).
Figure 26B:
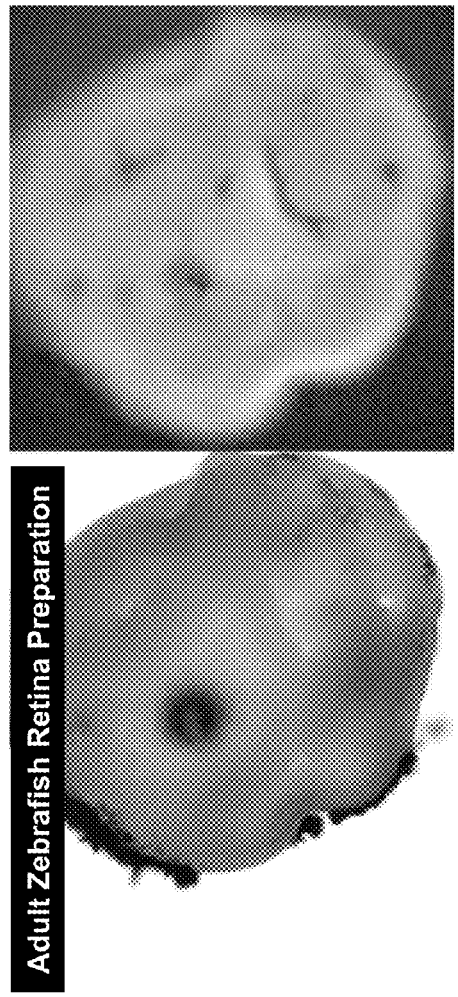
FIG. 26B is a pair of digital images of an adult zebrafish retina explant culture.

It was possible to optically image changes in neuronal calcium in intact live zebrafish larvae, as shown in FIGS. 25A-25C, brain slice preparations (FIG. 26A) and retinal preparations (FIG. 26B) as a means of testing the activity of BHQ-caged ATP, calcium, and neurotransmitters. The imaging methods were similar for all three preparations. Larvae or tissues, preloaded with a calcium indicator, were mounted in an imaging chamber in such a way as to prevent them from moving. Caged or uncaged compounds were perfused through the chamber at 8.3 μl/sec. 1PE uncaging in defined regions of tissue was induced using short bursts of UV light from a 405-nm laser. BHQ and CyHQ have sufficient sensitivity to 1PE at this wavelength for efficient uncaging.

2PE uncaging was performed using short bursts of 740-nm light directed at single cells. The laser power is kept below 7-10 mW to avoid tissue destruction at the beam focus. Changes in calcium indicator fluorescence were detected by confocal and two-photon FRET microscopy using a Statistical Optimization for the Analysis of Ratiometric Signals (SOARS) method as described in Broder et al., (2007) J. Opt. Soc. Am. A. Opt. Image Sci. Vis. 24: 2921-2931; Fan et al (2007) J. Biomedical Optics 12: 034017; and Xu et al., (2008) Nat. Neurosci. 11: 676-682, each of which is incorporated herein by reference in its entirety).

For high temporal resolution imaging, a single, two-dimensional focal plane was imaged at high speed (approximately 20 Hz) for the duration of the experiment. For volumetric imaging, three-dimensional volumes were imaged at approximately 1 Hz. A typical calcium imaging experiment generated approximately 4 Gb of data.

We claim:

1. A caged compound having the formula:

(I)

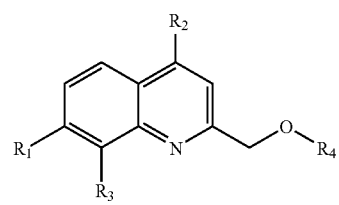

wherein $R_1$ is selected from the group consisting of: HO—, HS—, and (Me)$_2$N—;
$R_2$ is selected from the group consisting of: H and Cl;
$R_3$ is selected from the group consisting of: H, NO$_2$, CN, Cl, and Br; and
$R_4$ is a nucleoside phosphoester.

2. The caged compound of claim 1, wherein the nucleoside phosphoester is selected from the group consisting of: adenosine monophosphate (AMP), adenosine diphosphate (ADP), adenosine triphosphate (ATP), cytosine monophosphate (CMP), cytosine diphosphate (CDP), cytosine triphosphate (CTP), guanine monophosphate (GMP), guanine diphosphate (GDP), guanine triphosphate (GTP), thymidine monophosphate (TMP), thymidine diphosphate (TDP), and thymidine triphosphate (TTP).

3. The caged compound of claim 1, wherein, the caged compound has the characteristic that upon excitation with two photon laser excitation light energy the caged compound becomes uncaged.

4. The caged compound of claim 1 having the formula:

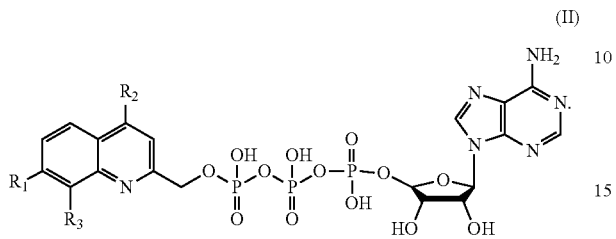

(II)

wherein $R_1$ is selected from the group consisting of: HO, HS, and $(Me)_2N$;
$R_2$ is selected from the group consisting of: H and Cl; and
$R_3$ is selected from the group consisting of: H, $NO_2$, and Br.

5. The caged compound of claim 1, wherein the compound is 8-bromo-7-hydroxyquinoline-ATP having the formula:

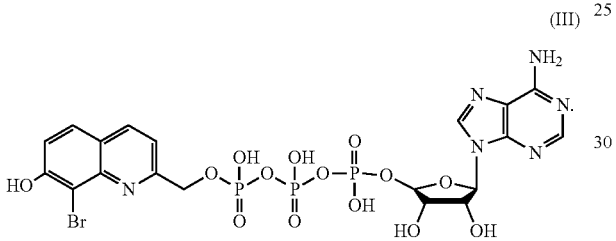

(III)

6. A method of synthesizing a caged nucleoside, comprising:
   (a) protecting the free hydroxy group of BHQ with a protecting group;
   (b) synthesizing a protected BHQ-alcohol;
   (c) synthesizing a protected BHQ-phosphate from the protected BHQ-alcohol, wherein the phosphate has protecting groups thereon;
   (d) removing the protecting groups from the protected BHQ-phosphate;
   (e) coupling of the BHQ-phosphate and an activated nucleotide; and
   (f) isolating a BHQ-nucleotide.

7. The method of claim 6, wherein the activated ADP is ADP-imidazolide and the BHQ-nucleotide is BHQ-ATP (III).

8. A method of detecting a biochemical or physiological reaction in a biological sample, comprising the steps of:
   (a) obtaining a biological sample;
   (b) delivering to the biological sample a caged compound, wherein the caged compound has the structure according to the formula:

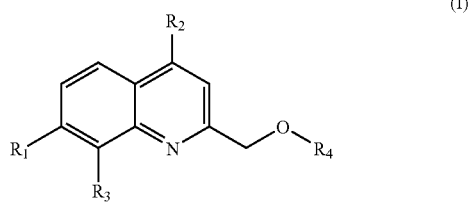

(I)

wherein $R_1$ is selected from the group consisting of: HO—, HS—, and $(Me)_2N$—;
$R_2$ is selected from the group consisting of: H and Cl;
$R_3$ is selected from the group consisting of: H, $NO_2$, CN, Cl, and Br; and
$R_4$ is a nucleoside phosphoester and wherein the nucleoside phosphester is selected from the group consisting of: adenosine monophosphate (AMP), adenosine diphosphate (ADP), adenosine triphosphate (ATP), cytosine monophosphate (CMP), cytosine diphosphate (CDP), cytosine triphosphate (CTP), guanine monophosphate (GMP), guanine diphosphate (GDP), guanine triphosphate (GTP), thymidine monophosphate (TMP), thymidine diphosphate (TDP), and thymidine triphosphate (TTP);
   (c) irradiating the biological sample with light energy, thereby dissociating the caged compound to provide an uncaged nucleotide that is capable of initiating a biochemical or physiological reaction in the biological sample; and
   (d) detecting the biochemical or physiological reaction in the biological sample.

9. The method of claim 8, further comprising the steps of:
   (i) contacting the biological sample with an indicator composition, wherein the indicator composition responds to the biochemical or physiological reaction by providing an detectable signal;
   (ii) allowing the indicator composition to emit a detectable signal; and
   (iii) detecting the emitted signal, thereby detecting the biochemical or physiological reaction.

10. The method of claim 8, wherein the physiological reaction generates an electrophysiological signal, and wherein the method further comprises the step of detecting the electrophysiological signal.

11. The method of claim 8, wherein the biological sample is selected from the group consisting of: an animal or a human subject, an isolated tissue sample, an isolated cell or population of cells, a cultured cell population, and a biological fluid.

12. The method of claim 8, wherein the indicator composition provides a detectable signal in response to the generation of a metabolite, wherein the generation of the metabolite is initiated by the uncaging of a caged nucleotide.

13. The method of claim 11, wherein the metabolite is selected from a metal ion, a nucleotide, and a compound transformed by the release of the uncaged nucleotide.

14. The method of claim 11, wherein the metabolite is a calcium ion.

15. The method of claim 8, wherein the caged compound is a caged nucleotide having the structure according to the formula:

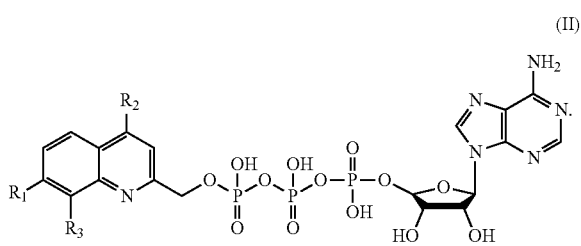

(II)

wherein $R_1$ is selected from the group consisting of: HO, HS, and $(Me)_2N$;

$R_2$ is selected from the group consisting of: H and Cl; and $R_3$ is selected from the group consisting of: H, $NO_2$, and Br.

16. The method of claim 15 wherein the caged compound is BHQ-ATP having the structure according to the formula:

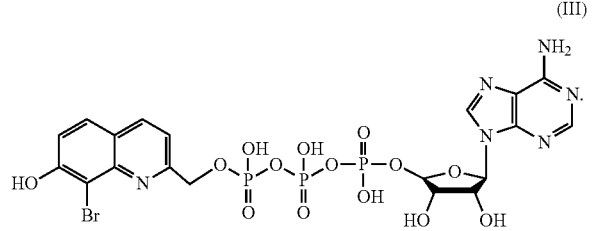

(III)

17. The method of claim 8, wherein the light energy irradiating the biological sample comprises a first laser light having a first wavelength and a second laser light having a second wavelength, thereby uncaging a target caged nucleotide by two photon laser excitation (2PE).

18. The method of claim 8, wherein the indicator composition emits a detectable signal in response to $Ca^{2+}$.

19. The method of claim 8, wherein the caged compound is delivered to the biological sample as a pharmaceutically acceptable composition, wherein the pharmaceutically acceptable composition comprises the gated compound and a pharmaceutically acceptable carrier.

20. A composition comprising a caged compound according to claim 1 and a pharmaceutically acceptable carrier.

* * * * *